(12) United States Patent
Folkman et al.

(10) Patent No.: US 8,173,433 B2
(45) Date of Patent: May 8, 2012

(54) PLATELET BIOMARKERS FOR CANCER

(75) Inventors: Judah M. Folkman, Brookline, MA (US); Giannoula Klement, Boston, MA (US); Tai-Tung Yip, Cupertino, CA (US); William E. Rich, Redwood Shores, CA (US); Vladimir N. Podust, Castro Valley, CA (US)

(73) Assignee: Vermillion, Inc., Fremont, CA (US)

( * ) Notice: Subject to any disclaimer, the term of this patent is extended or adjusted under 35 U.S.C. 154(b) by 588 days.

(21) Appl. No.: 11/658,377

(22) PCT Filed: Apr. 22, 2005

(86) PCT No.: PCT/US2005/013859
§ 371 (c)(1),
(2), (4) Date: Jun. 29, 2007

(87) PCT Pub. No.: WO2006/022895
PCT Pub. Date: Mar. 2, 2006

(65) Prior Publication Data
US 2009/0042229 A1 Feb. 12, 2009

Related U.S. Application Data

(60) Provisional application No. 60/598,387, filed on Aug. 2, 2004, provisional application No. 60/609,692, filed on Sep. 13, 2004, provisional application No. 60/634,148, filed on Dec. 7, 2004.

(51) Int. Cl.
*G01N 33/48* (2006.01)
*A61K 35/14* (2006.01)

(52) U.S. Cl. .......................................... 436/64; 530/380

(58) Field of Classification Search .................. None
See application file for complete search history.

(56) References Cited

U.S. PATENT DOCUMENTS
2006/0134605 A1  6/2006  Folkman et al.

OTHER PUBLICATIONS

Salven et al. Serum VEGF Levels in Women With a Benign Breast Tumor or Breast Cancer; Breast Cancer Research and Treatment, vol. 53 (1999) pp. 161-166.*
Dosquet et al. Are Angiogenic Factors, Cytokines, and Soluble Adhesion Molecules Prognostic Factors in Patients With Renal Cell Carcinoma?; Clinical Cancer Research, vol. 3 (1997) pp. 2451-2458.*
Lissoni et al. Chemotherapy and Angiogenesis in Advanced Cancer: Vascular Endothelial Growth Factor (VEGF) Decline As Predictor of Disease Control During Taxol Therapy in Metastatic Breast Cancer; The International Journal of Biological Markers, vol. 15, No. 4 (2000) pp. 308-311.*
Grisaru et al. Connective Tissue Activating Protein Peptide III Expression Disappears Progressively With Increased Dysplasia in Human Cervical Epithelium; Gynecologic Oncology, vol. 79 (2000) pp. 23-27.*
Kurimoto et al. Plasma Platelet-Derived Growth Factor-B Chain Is Elevated in Patients With Extensively Large Brain Tumor; Acta Neurochirurgica, vol. 137 (1995) pp. 182-187.*
Issaq et al. The SELDI-TOF MS Approach to Proteomics: Protein Profiling and Biomarker Identification; Biochemical and Biophysical Research Communications, vol. 292 (2002) pp. 587-592.*
Sluitz et al. Serum Evaluation of Basic Fibroblast Growth Factor in Cervical Cancer Patients; Cancer Letters, vol. 94 (1995) pp. 227-231.*
Yamamoto et al. Concentrations of Vascular Endothelial Growth Factor in the Sera of Normal Controls and Cancer Patients; Clinical Cancer Research, vol. 2 (1996) pp. 821-826.*
Yamamoto et al. Expression of Vascular Endothelial Growth Factor (VEGF) in Epithelial Ovarian Neoplasms: Correlation With Clinicopathology and Patient Survivial, and Analysis of Serum VEGF Levels; British Journal of Cancer, vol. 76, No. 9 (1997) pp. 1221-1227.*
Bentas et al. Serum Levels of Basic Fibroblast Growth Factor Reflect Disseminated Disease in Patients With Testicular Germ Cell Tumors; Urology Research, vol. 30 (2003) pp. 390-393.*
Feldman et al. A Prospective Analysis of Plasma Endostatin Levels in Colorectal Cancer Patients With Liver Metastases; Annals of Surgical Oncology, vol. 8, No. 9 (2001) pp. 741-745.*
Hamano et al. Physiological Levels of Tumstatin, A Fragment of Collagen IV ALPHA3 Chain, Are Generated by MMP-9 Proteolysis and Suppress Angiogenesis Via Alpha V Beta 3 Integrin; Cancer Cell, vol. 3, No. 6 (2003) pp. 589-601.*
Leitzel et al. Elevated Plasma Platelet-Derived Growth Factor B-Chain Levels in Cancer Patients; Cancer Research, vol. 51 (1991) pp. 4149-4154.*
Manenti et al. Expression Levels of Vascular Endothelial Growth Factor, Matrix Metalloproteinases 2 and 9 ANT Tissue Inhibitor of Metalloproteinsases 1 and 2 in the Plasma of Patients With Ovarian Carcinoma; European Journal of Cancer, vol. 39 (2003) pp. 1948-1956.*
Slaton et al. Expression Levels of Genes That Regulate Metastasis an Angiogenesis Correlate With Advanced Pathological Stage of Renal Cell Carcinoma; American Journal of Pathology, vol. 158, No. 2 (2001) pp. 735-743.*
Wright et al. Elevated Apolipoprotein(A) Levels in Cancer Patients; International Journal of Cancer, vol. 43 (1989) pp. 241-244.*
Caine et al. Platelet-Derived VEGF, FLT-1, Angiopoietin-1 and P-Selectin in Breast and Prostate Cancer: Further Evidence for a Role of Platelets in Tumour Angiogenesis; Annals of Medicine, vol. 36 (Jan. 2004) pp. 273-277.*
Salven et al. Leukocytes and Platelets of Patients With Cancer Contain High Levels of Vascular Endothelial Growth Factor; Clinical Cancer Research, vol. 5 (1999) pp. 487-491.*
Sierko et al. Platelets and Angiogenesis in Malignancy; Seminars in Thrombosis and Hemostasis, vol. 30, No. 1 (Feb. 2004) pp. 95-108.*
Robert Salgado et al., "Platelets and vascular endothelial growth factor (VEGF): A morphological and functional study", Angiogenesis 4: 37-43, 2001.

* cited by examiner

*Primary Examiner* — Rebecca Prouty
*Assistant Examiner* — Paul Martin
(74) *Attorney, Agent, or Firm* — Stephen A Bent; Foley & Lardner LLP

(57) ABSTRACT

The present invention relates to the fields of immunology and biochemistry. Particularly, the present invention describes methods, devices and kits for early detection of clinical conditions having associated changes in systemic angiogenic activity, particularly cancers, inflammatory conditions, infections, and events associated with pregnancy and abortion.

5 Claims, 23 Drawing Sheets

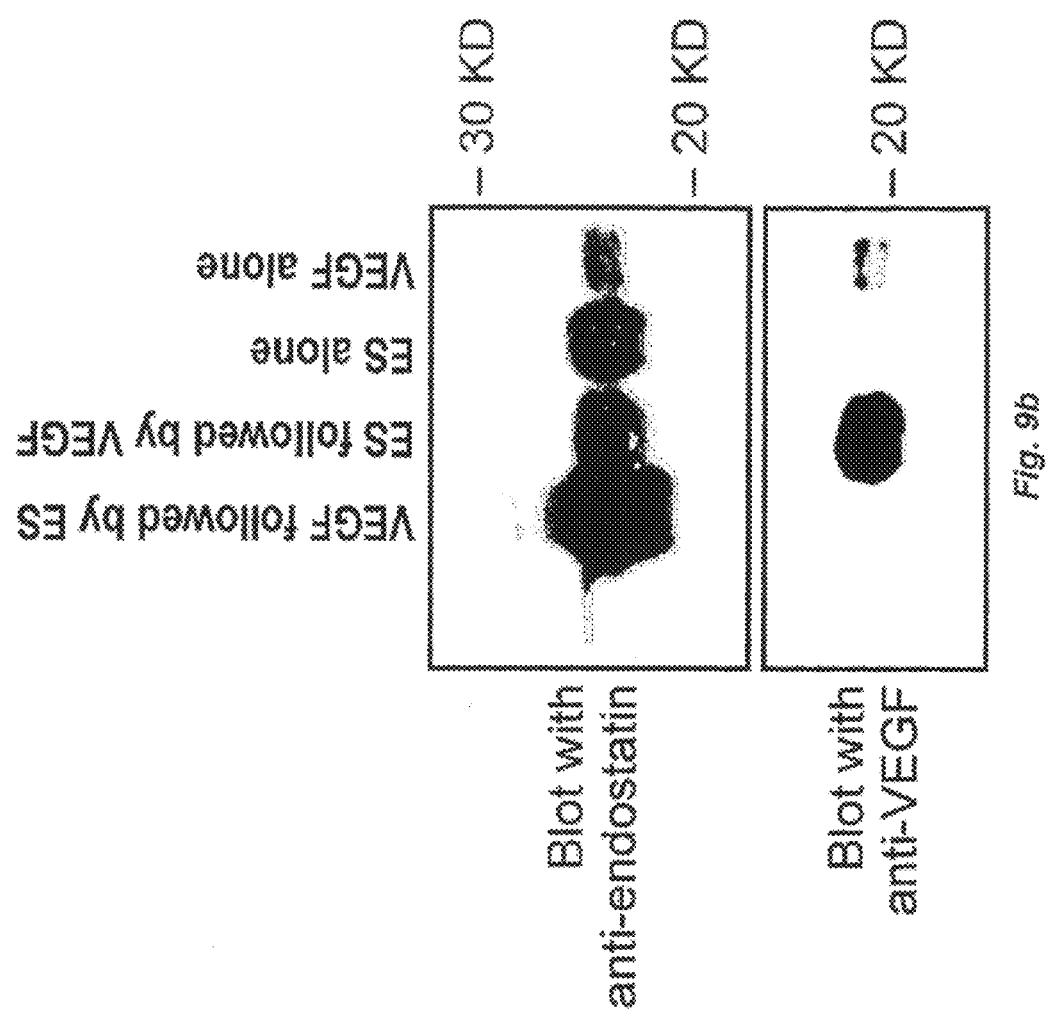

PLATELET BIOMARKERS FOR CANCER

FIELD OF THE INVENTION

The present invention relates to the fields of immunology and biochemistry. Particularly, the present invention describes methods, devices and kits for early detection of clinical conditions having associated changes in systemic angiogenic activity, particularly cancers, inflammatory conditions, infections, and events associated with pregnancy.

BACKGROUND OF THE INVENTION

Angiogenesis, the formation of new capillary blood vessels, is a fundamental process essential for reproduction, embryonic development, and cancer growth and progression. The major route of tumor spread is through the bloodstream. Once in circulation, the tumor cells aggregate in clumps with platelets, which enhances the tumor cell survival. The tumor emboli will then adhere to the blood vessel endothelium. See, e.g., Bikfalvi et al., *Semin Thromb Hemost.*, 30(1):137-44 (2004); Sargiannidou et al., *Semin Thromb Hemost.*, 30(1): 127-36 (2004); Sierko et al., *Semin Thromb Hemost.*, 30(1): 95-108 (2004); Blakytny et al., *J Cell Physiol.*, 199(1):67-76 (2004); Folkman J., *Semin Oncol.*, 29 (6 Suppl 16):15-8 (2002).

Early detection of a disease condition such as cancer typically allows for a more effective therapeutic treatment with a correspondingly more favorable clinical outcome. Thus, there is a need for detection methods which allow clinicians to determine the presence of cancers and tumors before advanced stages of cancerous diseases are reached. Moreoever, clinicians need methods for efficiently and accurately determining whether cancerous tumors are dormant or malignant.

SUMMARY OF THE INVENTION

The present invention allows for the detection and differentiation of conditions associated with angiogenesis and, in particular, cancer. The invention involves the use of biomolecules found in blood platelets as biomarkers for clinical conditions relating to angiogenesis status and, in particular, cancer status. As used herein, angiogenic status includes, but is not limited to, distinguishing between disease versus non-disease states such as cancer versus normal (i.e., non-cancer) and, in particular, aggressive cancer versus dormant cancer or aggressive cancer versus non-cancer.

In fact, it has surprisingly been found that a number of the biomarkers of the present invention can be used to distinguish between benign versus malignant tumors, aggressive versus dormant tumors, angiogenic versus non-angiogenic tumors, etc. The selective uptake of angiogenic regulators by platelets, without a corresponding increase of these proteins in plasma, provides a useful measurement to aid in the diagnosis, particularly the early diagnosis, of cancer before a tumor is clinically detected. Moreover, it has been found that the multiplexed measurement of a plurality of biomarkers in platelets, i.e., platelet profiling, provides a very sensitive indication of alterations in angiogenic activity in a patient, and provides disease specific identification. Such platelet properties can be used to detect human cancers of a microscopic size that are undetectable by any presently available diagnostic method. Even a small source of angiogenic proteins, such as a dormant non-angiogenic tumor can modify the protein profile detectably before the tumor itself can be clinically detected. In certain embodiments, the platelet angiogenic profile is more inclusive than a single biomarker because it can detect a wide range of tumor types and tumor sizes. Relative changes in the platelet angiogenic profile permit the tracking of a tumor throughout its development, beginning from an early in situ cancer, i.e., beginning from a point before the tumor is detected clinically, allowing for rapid prognosis, early treatment, and precise monitoring of disease progression or regression (e.g., following treatment with non-toxic drugs such as angiogenesis inhibitors).

Platelets uptake many of the known angiogenic regulatory proteins, e.g., positive regulators such as VEGF-A, VEGF-C, bFGF, HGF, Angiopoietin-1, PDGF, EGF, IGF-1, IGF BP-3, Vitronectin, Fibronectin, Fibrinogen, Heparanase, and Sphingosine-1 $PO_4$, and/or negative regulators such as Thrombospondin, the NK1/NK2/NK3 fragments of HGF, TGF-beta-1, Plasminogen(angiostatin), High molecular weight kininogen (domain 5), Fibronection(45 kDfragment), EGF (fragment), Alpha-2 antiplasmin(fragment), Beta-thromboglobulin, Endostatin and BDNF (brain derived neurotrophicfactor), and continue to sequester them for as long as the source (e.g., a tumor) exists. Without limiting the invention to any particular biological mechanism or role for the sequestration of angiogenic regulators, platelets are believed to act as efficient transporters of these proteins to sites of activated endothelium and the profile of biomarkers in the platelets reflects the onset of tumor presence and growth.

As such, in one aspect, the present invention provides a method for qualifying angiogenic status in a subject, the method comprising: (a) measuring at least one platelet-associated biomarker in a biological sample from the subject, wherein the at least one platelet-associated biomarker is selected from the group consisting of the biomarkers of Table 1 and Table 2, supra; and (b) correlating the measurement with angiogenic status. In a preferred embodiment, the at least one platelet-associated biomarker is selected from the group consisting of the biomarkers of Table 1.

In a preferred embodiment, the at least one platelet-associated biomarker is selected from the following biomarkers: VEGF, PDGF, bFGF, PF4, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin.

In one embodiment, the at least one platelet-associated biomarker is measured by capturing the biomarker on an adsorbent of a SELDI probe and detecting the captured biomarkers by laser desorption-ionization mass spectrometry. In certain embodiments, the adsorbent is a cation exchange adsorbent, an anion exchange adsorbent, a metal chelate or a hydrophobic adsorbent. In other embodiments, the adsorbent is a biospecific adsorbent. In another embodiment, the at least one platelet-associated biomarker is measured by immunoassay.

In another embodiment, the correlating is performed by a software classification algorithm. In certain embodiments, the angiogenic status is cancer versus normal (non-cancer). In another embodiment, the angiogenic status is benign tumor versus malignant tumor. In yet another embodiment, the angiogenic status is aggressive tumor versus non-aggressive, i.e., dormant, tumor. In yet another embodiment, the angiogenic status is a particular type of cancer, including breast cancer, liver cancer, lung cancer, hemangioblastomas, bladder cancer, prostate cancer, gastric cancer, cancers of the brain, neuroblastomas, colon cancer, carcinomas, sarcomas, leukemia, lymphoma and myolomas.

In yet another embodiment, the method further comprises: (c) managing subject treatment based on the angiogenic status. If the measurement correlates with cancer, then managing subject treatment comprises administering, for example, a chemotherapeutic agent to the subject.

In a further embodiment, the method further comprises: (d) measuring the at least one platelet-associated biomarker after subject management.

In another aspect, the present invention provides a method comprising measuring at least one biomarker in a sample from a subject, wherein the at least one platelet-associated biomarker is selected from the group consisting of the biomarkers set forth in Table 1 or 2. In a preferred embodiment, the at least one platelet-associated biomarker is selected from the group consisting of the biomarkers of Table 1.

In one embodiment, the at least one platelet-associated biomarker is measured by capturing the biomarker on an adsorbent of a SELDI probe and detecting the captured biomarkers by laser desorption-ionization mass spectrometry. In certain embodiments, the adsorbent is a cation exchange adsorbent, an anion exchange adsorbent, a metal chelate or a hydrophobic adsorbent. In other embodiments, the adsorbent is a biospecific adsorbent. In another embodiment, the at least one platelet-associated biomarker is measured by immunoassay.

In still another aspect, the present invention provides a kit comprising: (a) a solid support comprising at least one capture reagent attached thereto, wherein the capture reagent binds at least one platelet-associated biomarker from a first group consisting of the biomarkers set forth in Table 1 and Table 2; and (b) instructions for using the solid support to detect the at least one biomarker set forth in Table 1 and Table 2. In a preferred embodiment, the at least one platelet-associated biomarker is selected from the group consisting of the biomarkers of Table 1. In another preferred embodiment, the at least one platelet-associated biomarker is selected from the group consisting of the following biomarkers: VEGF, PDGF, bFGF, PF4, CTAPIII, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin and combinations thereof.

In one embodiment, the kit provides instructions for using the solid support to detect a biomarker selected from the following biomarkers: VEGF, PDGF, bFGF, PF4, CTAPIII, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin and combinations thereof.

In another embodiment, the solid support comprising the capture reagent (also referred to as an affinity reagent) is a SELDI probe. In certain embodiments, the capture reagent is a cation exchange adsorbent, an anion exchange adsorbent, a metal chelate or a hydrophobic adsorbent. In some preferred embodiments, the capture reagent is a cation exchange adsorbent. In other embodiments, the kit additionally comprises (c) an anion exchange chromatography sorbent, such as a quaternary amine sorbent (e.g., BioSepra Q Ceramic HyperD® F sorbent beads). In other embodiments, the kit additionally comprises (c) a container containing at least one of the platelet-associated biomarkers of Table 1 and Table 2.

In a further aspect, the present invention provides a kit comprising: (a) a solid support comprising at least one capture reagent attached thereto, wherein the capture reagent binds at least one platelet-associated biomarker from a first group consisting of the biomarkers set forth in Table 1 and Table 2; and (b) a container comprising at least one of the biomarkers set forth in Table I or Table II. In a preferred embodiment, the platelet-associated biomarker is selected from the group consisting of the biomarkers of Table 1.

In one embodiment, the kit provides instructions for using the solid support to detect a biomarker selected from the following biomarkers: VEGF, PDGF, bFGF, PF4, CTAPIII, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin. In another embodiment, the kit provides instructions for using the solid support to detect each of the following biomarkers: VEGF, PDGF, bFGF, PF4, CTAPIII, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin or, alternatively, additionally detecting each of these biomarkers.

In another embodiment, the solid support comprising the capture reagent is a SELDI probe. In certain embodiments, the capture reagent is a cation exchange adsorbent, an anion exchange adsorbent, a metal chelate or a hydrophobic adsorbent. In other embodiments, the adsorbent is a biospecific adsorbent. In some embodiments, the capture reagent is a cation exchange adsorbent. In other embodiments, the kit additionally comprises (c) an anion exchange chromatography sorbent.

In yet a further aspect, the present invention provides a software product, the software product comprising: (a) code that accesses data attributed to a sample, the data comprising measurement of at least one platelet-associated biomarker in the biological sample, the platelet-associated biomarker selected from the group consisting of the biomarkers of Table 1 and Table 2; and (b) code that executes a classification algorithm that classifies the angiogenic disease status of the sample as a function of the measurement. In a preferred embodiment, the biomarker is selected from the group consisting of the biomarkers of Table 1.

In yet another embodiment, the invention provides a method for determining the course of tumor progression or regression in a subject, comprising measuring, at a first time, at least one biomarker in a sample of platelets from a subject, wherein the at least one biomarker is selected from the group consisting of VEGF, PDGF, bFGF, PF4, CTAPIII, endostatin, tumstatin, tissue inhibitor of metalloprotease, apolipoprotein A1, IL8, TGF, NGAL, MP, metalloproteases, BDNF, NGF, CTGF, angiogenin, angiopoietins, angiostatin, and thrombospondin; and measuring, at a second time, the at least one biomarker in a sample of platelets from the subject; and comparing the first measurement and the second measurement; wherein the comparative measurements determine the course of tumor progression or regression in a subject.

In one embodiment, the classification algorithm classifies angiogenic status of the sample as a function of the measurement of a biomarker selected from the group consisting of VEGF, PDGF, bFGF, PF4, CTAPIII, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin. In another embodiment, the classification algorithm classifies angiogenic status of the sample as a function of the measurement of each of the following biomarkers: VEGF, PDGF, bFGF, PF4, endostatin, tumstatin, tissue inhibitor of metalloprotease, apolipoprotein A1, IL8, TGF, NGAL, MIP, metalloproteases, BDNF, NGF, CTGF, angiogenin, angiopoietins, angiostatin, and thrombospondin.

In other aspects, the present invention provides purified biomolecules selected from the platelet-associated biomarkers set forth in Table 1 and Table 2 and, additionally, methods comprising detecting a biomarker set forth in Table 1 or Table 2 by mass spectrometry or immunoassay.

Other features, objects and advantages of the invention and its preferred embodiments will become apparent from the detailed description, examples and claims that follow.

BRIEF DESCRIPTION OF THE DRAWINGS

FIG. 9b shows that endostatin competes with VEGF for uptake into platelet cells.

FIG. 12a shows the intracellular distribution of VEGF in platelets. FIG. 12a panel 1: platelets are stained with phalloidin. FIG. 12a panel 2: platelets are stained with anti-VEGF. FIG. 12a panel 3: overlay. FIG. 12c shows the intracellular distribution of VEGF (FIG. 12c panel 1), vWF (FIG. 12c panel 2) and overlay (FIG. 12c panel 3) in platelets and megakaryocytes.

DETAILED DESCRIPTION OF THE INVENTION AND PREFERRED EMBODIMENTS

I. Introduction

Figure 1A:
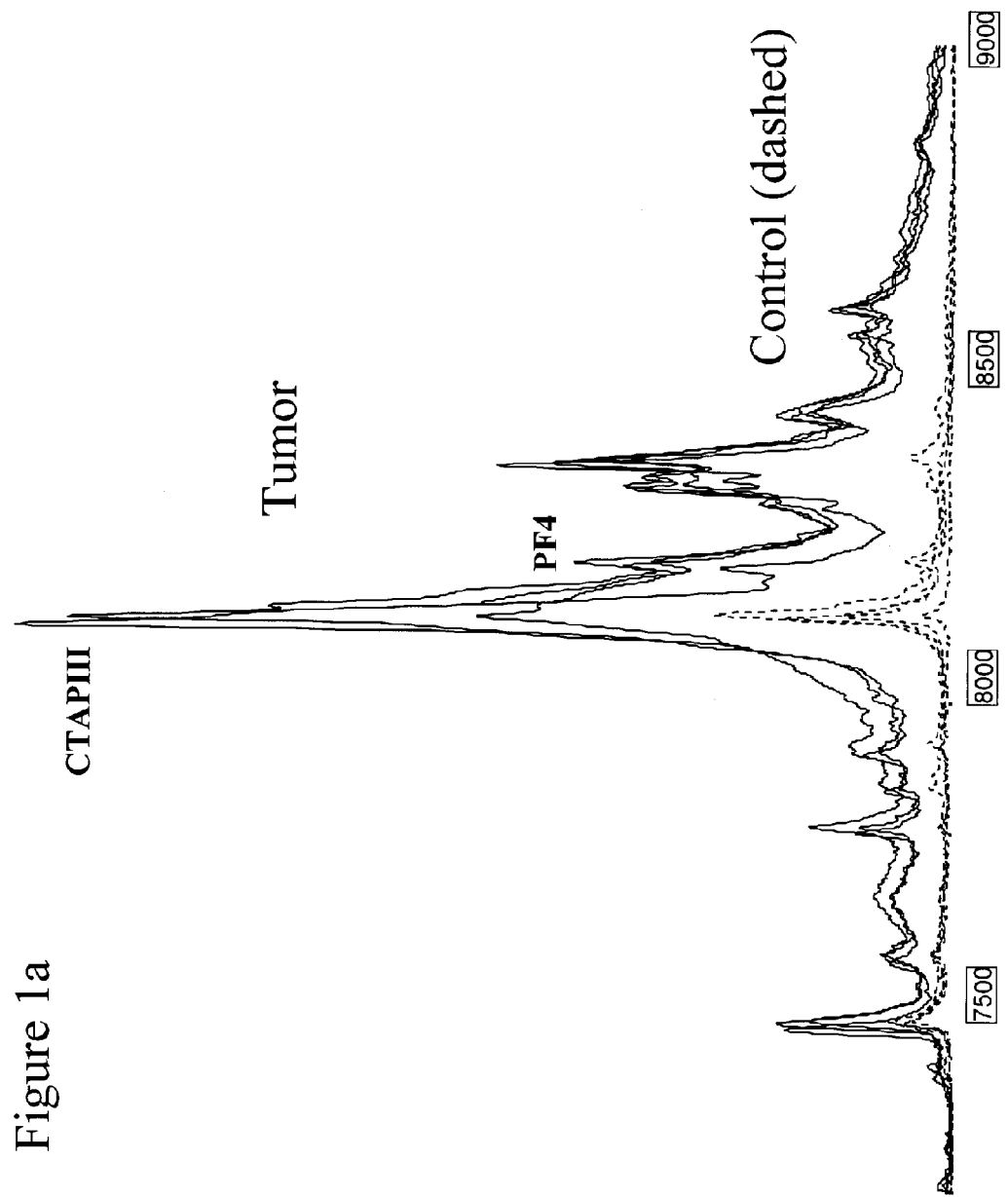
FIG. 1a shows a mass spectrophotometric expression map of platelet extracts taken from control animals (dashed lines) and animals implanted with dormant tumors (black lines). The numbers on the x-axis refer to the mass to charge ratios (m/z) of the observed particles and the heights of the curves correspond to the intensity of the observed peaks. The extracts used were obtained from fraction 2 of the initial anion exchange fractionation, as described in the Examples. Samples from this fraction were analyzed on the WCX2 PROTEINCHIP array. CTAPIII and PF4 were identified to be up-regulated in tumor-bearing mice.
Figure 1B:
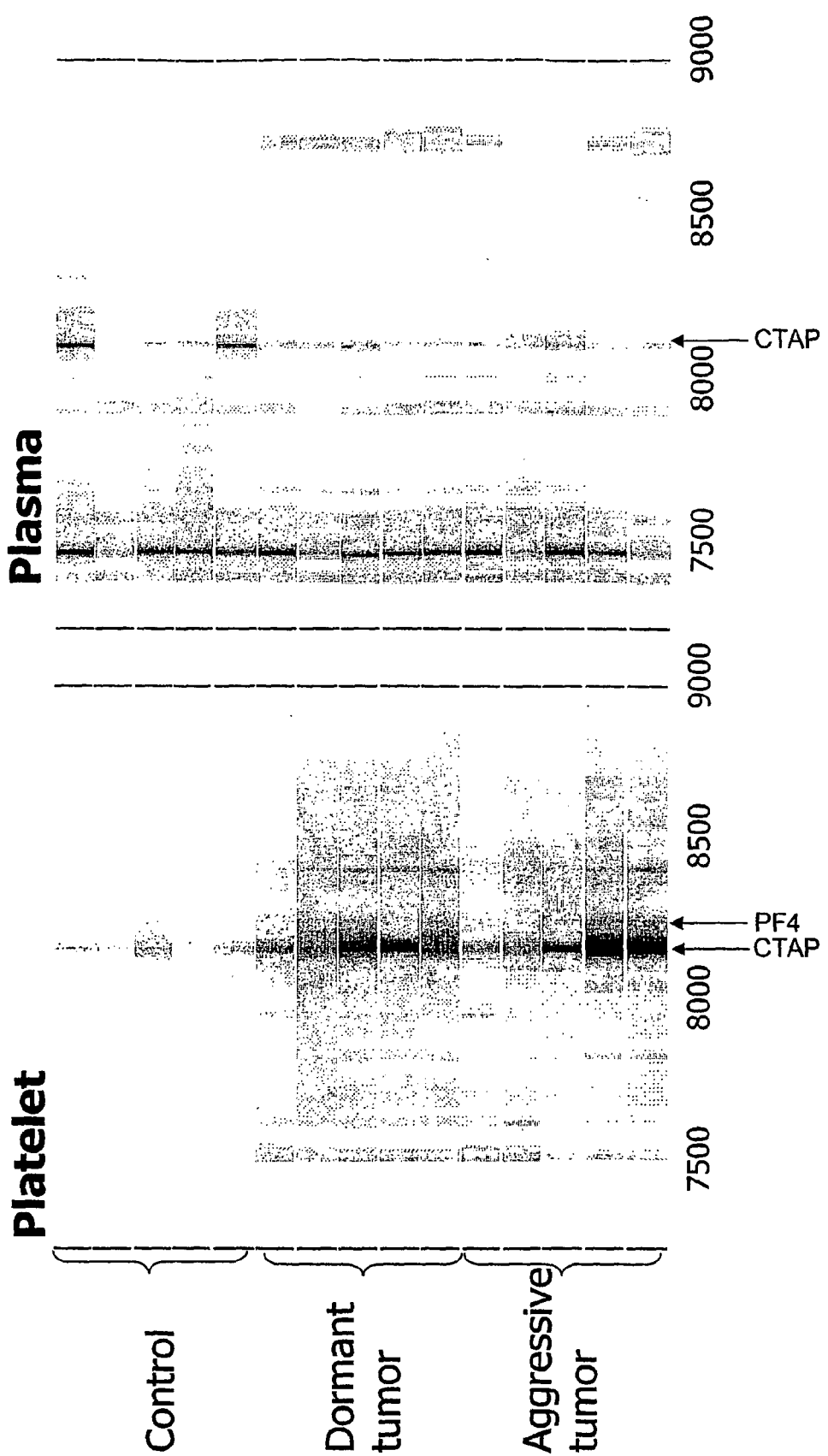
FIG. 1b shows that CTAPIII and PF4 (arrows) were up-regulated in platelets of both dormant and angiogenic tumor-bearing mice, but not in plasma.
Figure 2A:
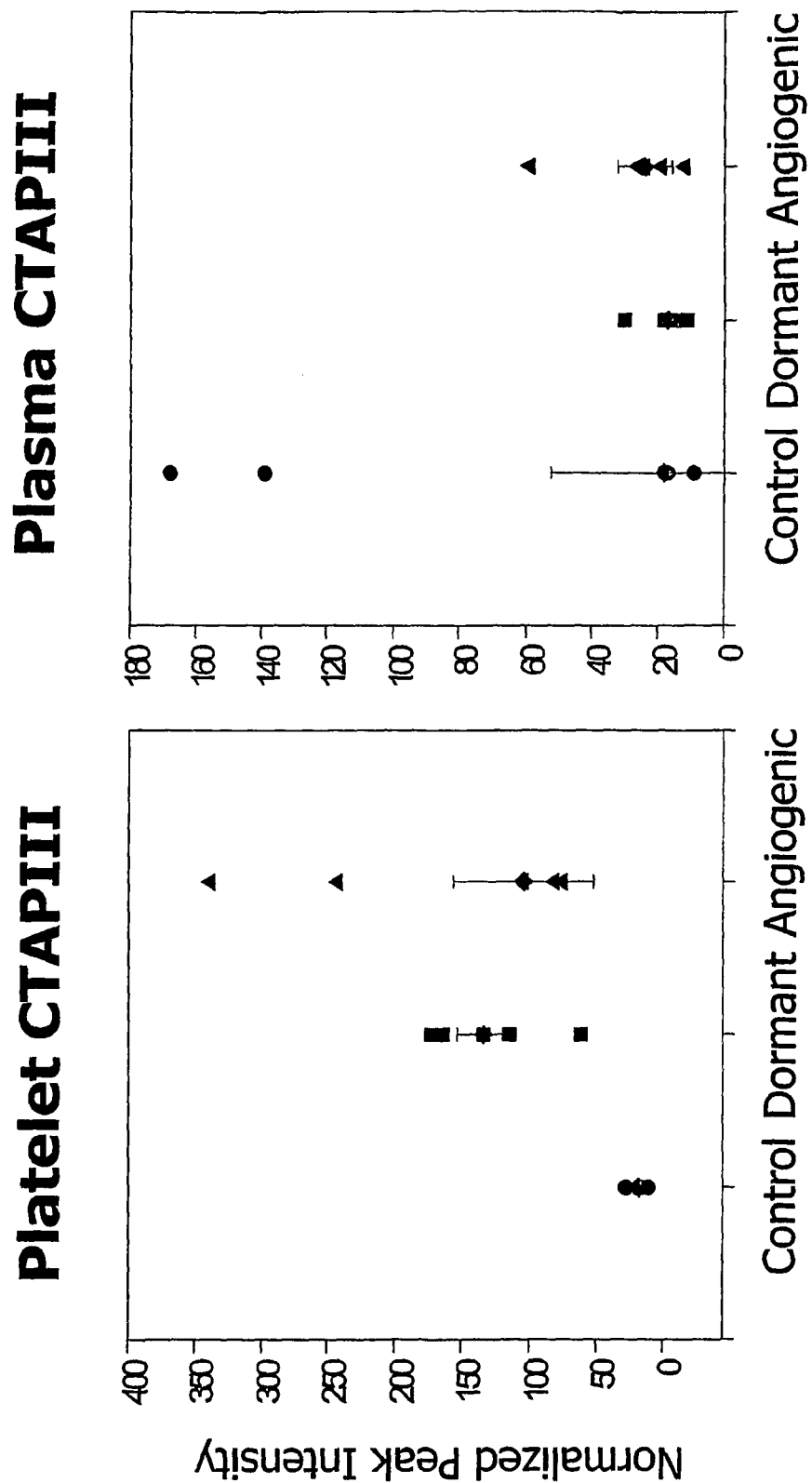
FIG. 2a shows a plot of the normalized CTAPIII peak intensity measured in extracts taken from the platelets and plasma of three groups of mice: control individuals, and individuals with dormant (non-angiogenic) and aggressive (angiogenic) human liposarcoma tumors, respectively.
Figure 2B:
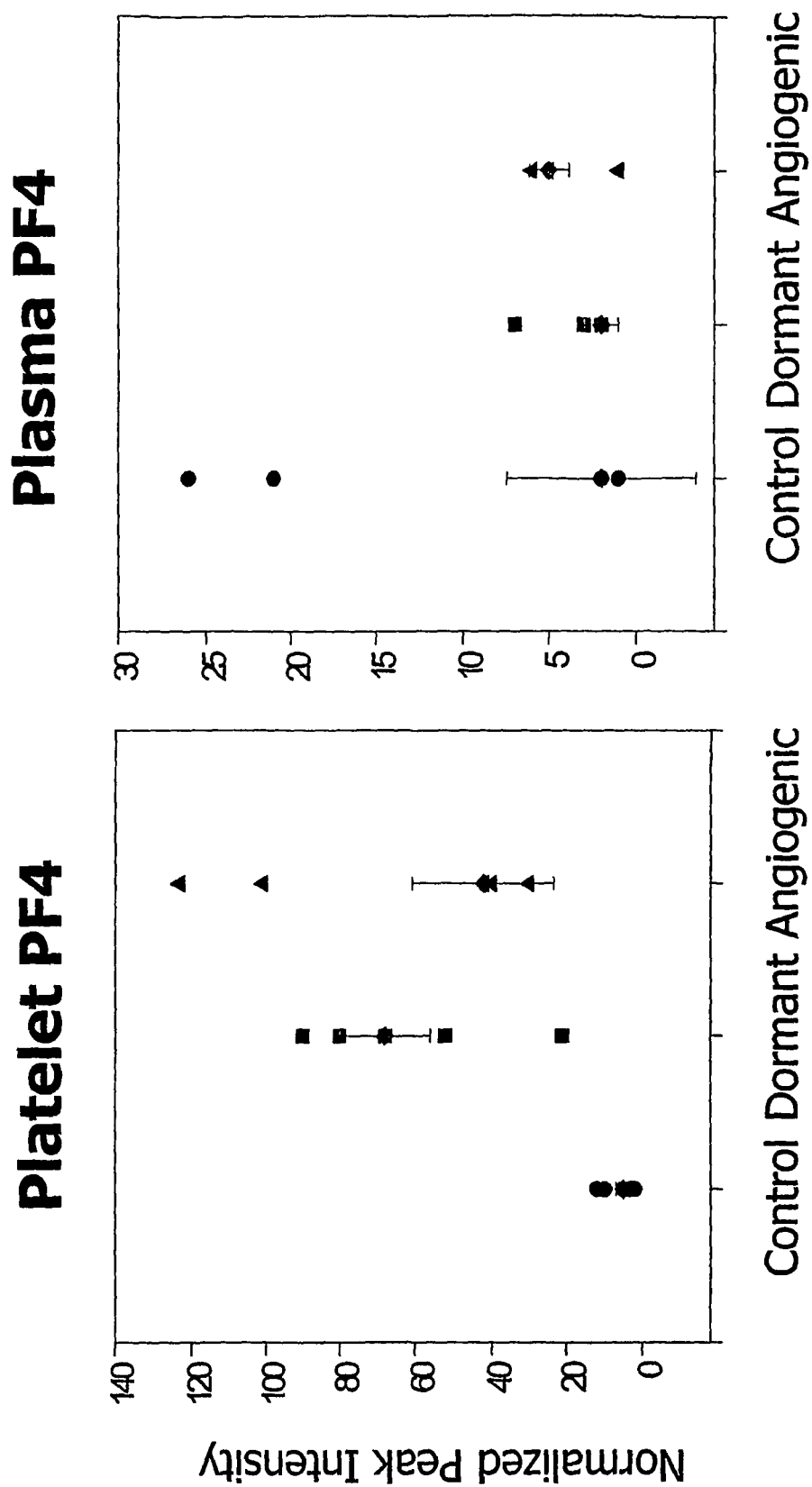
FIG. 2b shows a plot of the normalized PF4 peak intensity in platelets and plasma of the same groups of mice.
Figure 2C:
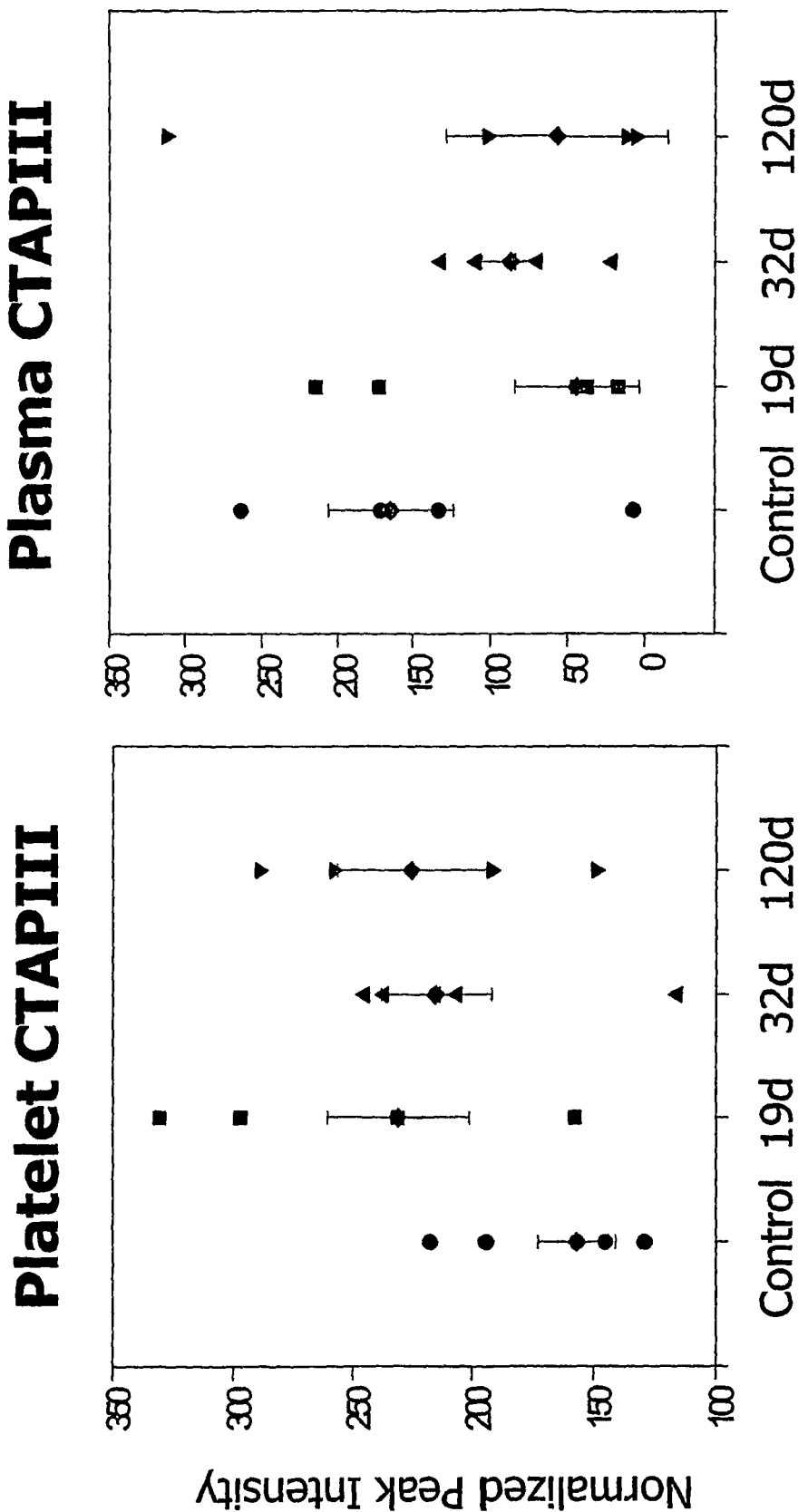
FIG. 2c shows a plot of the normalized CTAPIII peak intensity in the platelets and plasma of tumor-bearing mice at 19 days, 32 days and 120 days of growth, indicating that platelet CTAP III levels increased over the time course studied, while plasma CTAP III levels decreased, or did not change, over the same period.
Figure 2D:
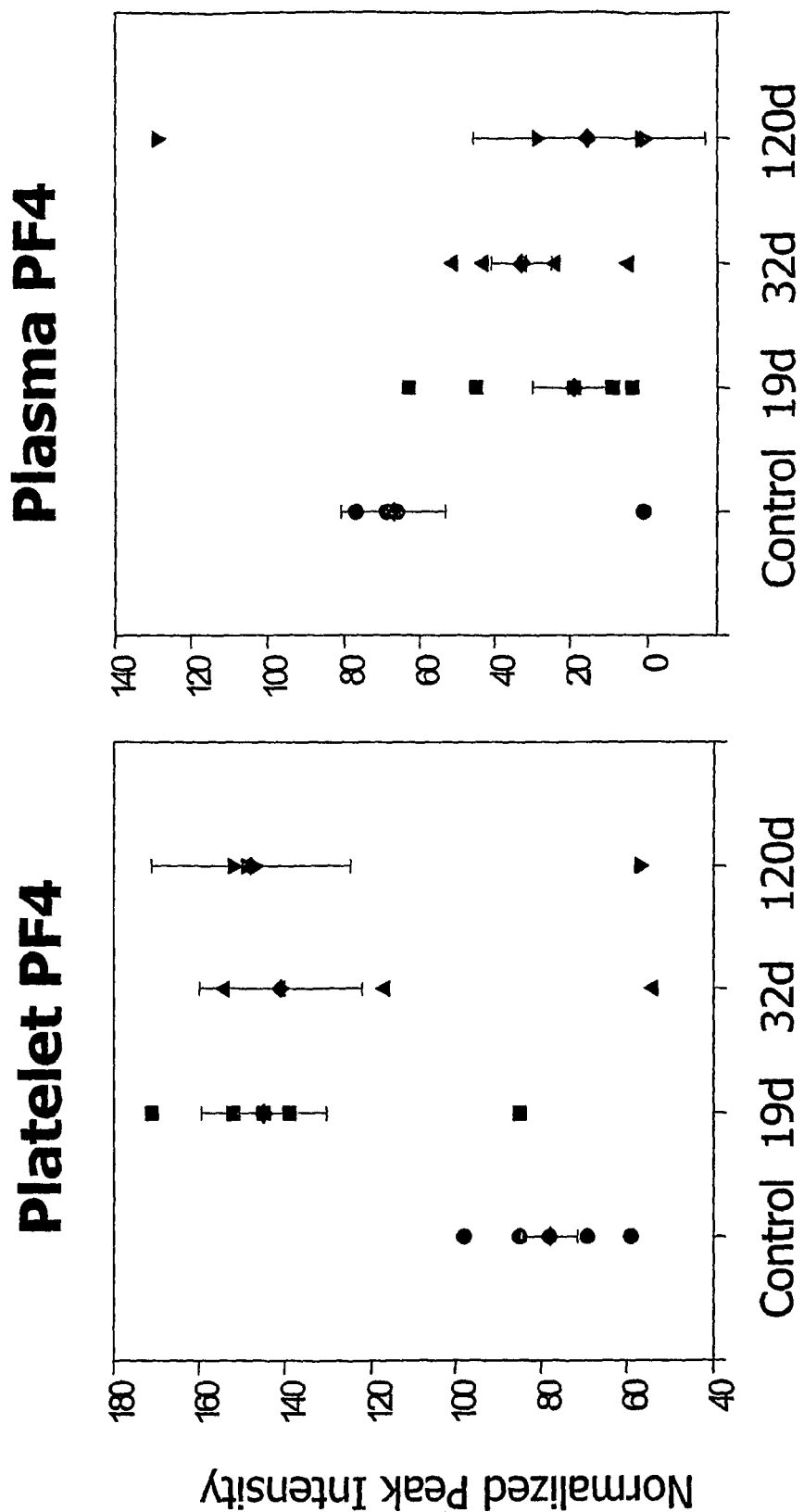
FIG. 2d shows a plot of the normalized PF4 peak intensity in platelets and plasma of tumor-bearing mice at 19 days, 32 days and 120 days of growth, indicating that platelet PF4 levels increased over the time course studied, while plasma PF4 levels decreased, or did not change, over the same period. The median±standard errors are shown for each group of peak intensities in FIG. 2.
Figure 3A:
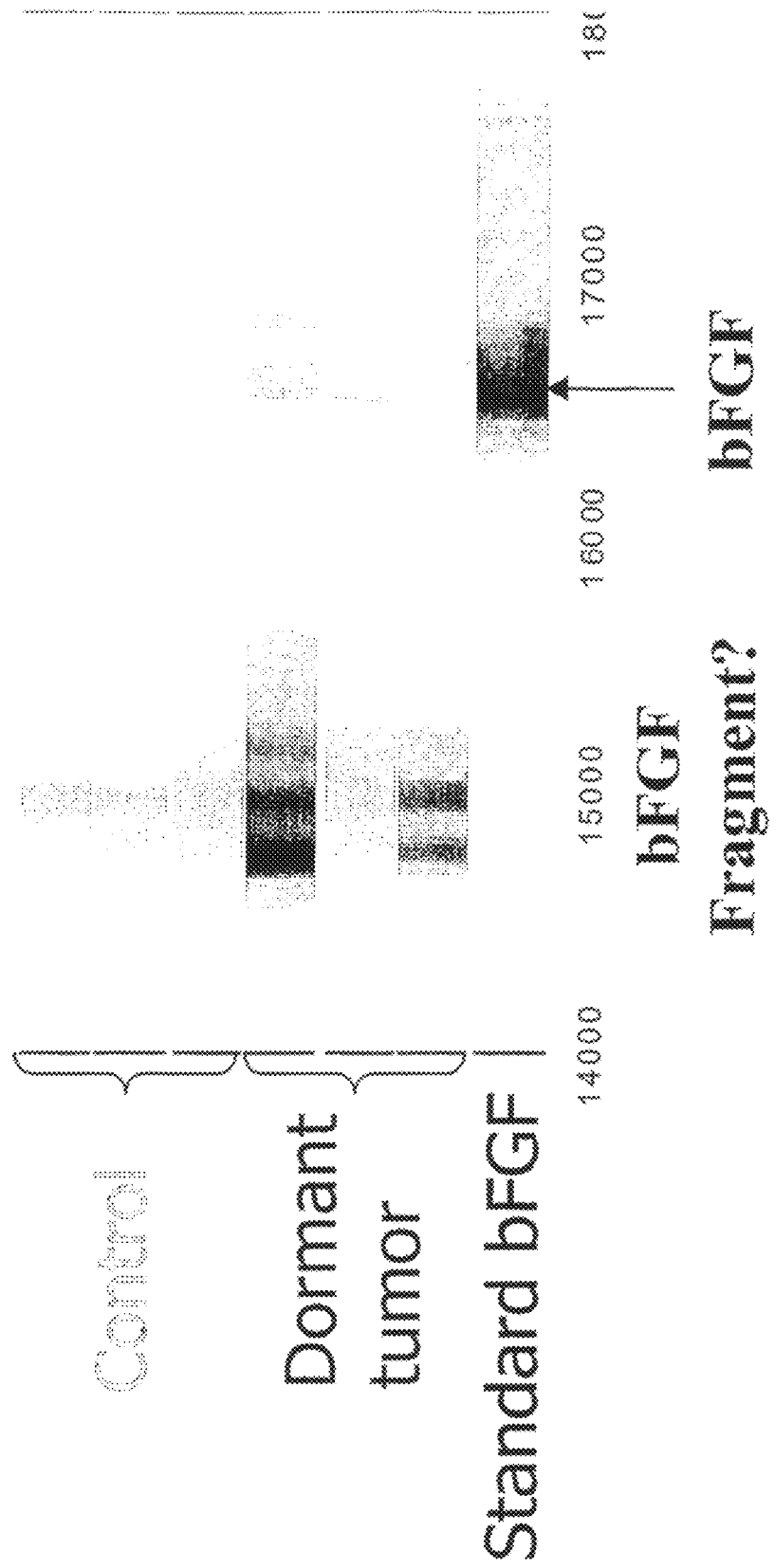
FIG. 3a shows an antibody interaction discovery map of platelet and plasma extracts, using an anti-basic fibroblast growth factor (anti-bFGF) antibody. Specifically, the figure shows that bFGF and fragments thereof are up-regulated in platelets of dormant (non-angiogenic) tumor-bearing mice.
Figure 3B:
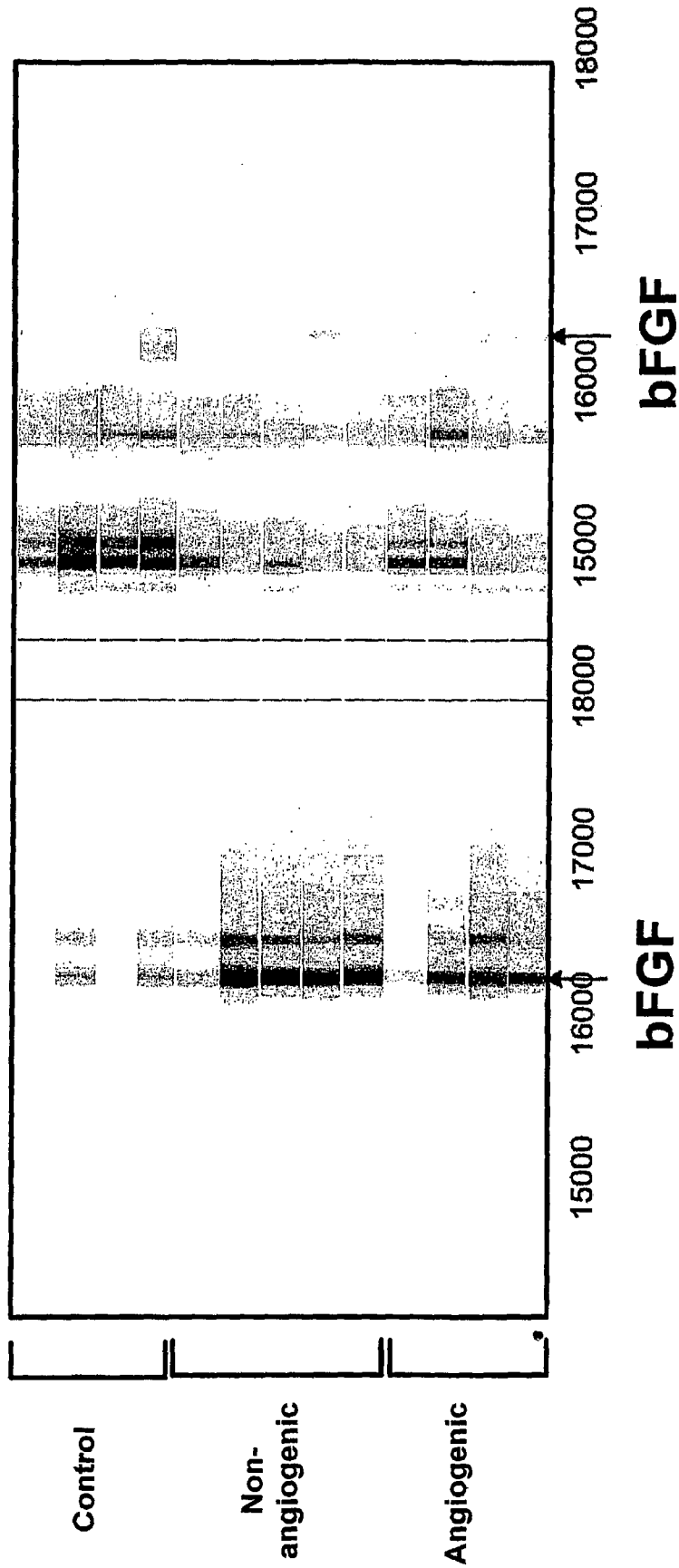
FIG. 3b shows an expresion map which allows comparison of the changing expression levels in platelet versus plasma extracts, in addition to differences between expression in bFGF in non-angiogenic and angiogenic tumor bearing mice.
Figure 3C:
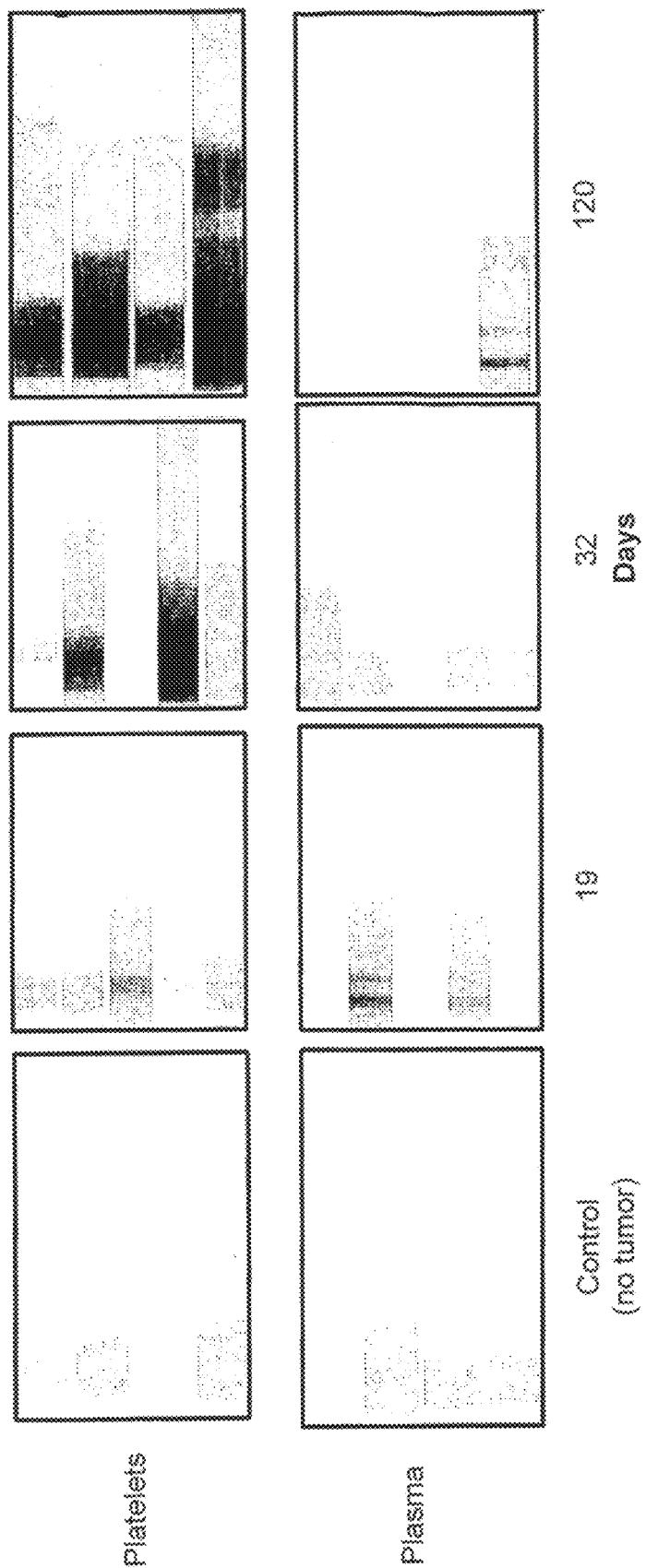
FIG. 3c shows a time course of bFGF sequestration in platelets.
Figure 4A:
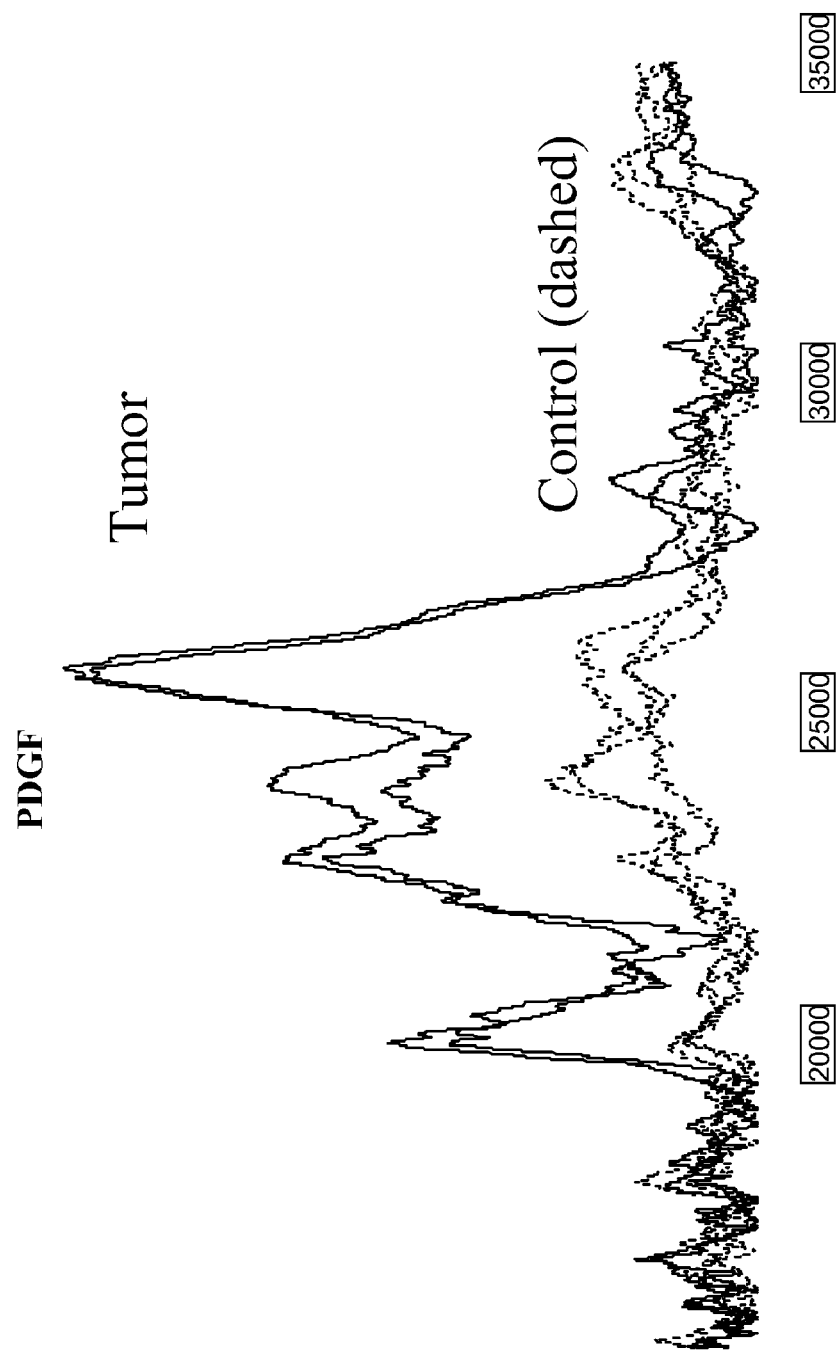
FIG. 4a shows an antibody interaction discovery map of platelet extracts, using an anti-platelet derived growth factor (anti-PDGF) antibody. The figure shows that PDGF and fragments thereof are up-regulated in dormant tumor-bearing mice (30 days after implantation).
Figure 4B:
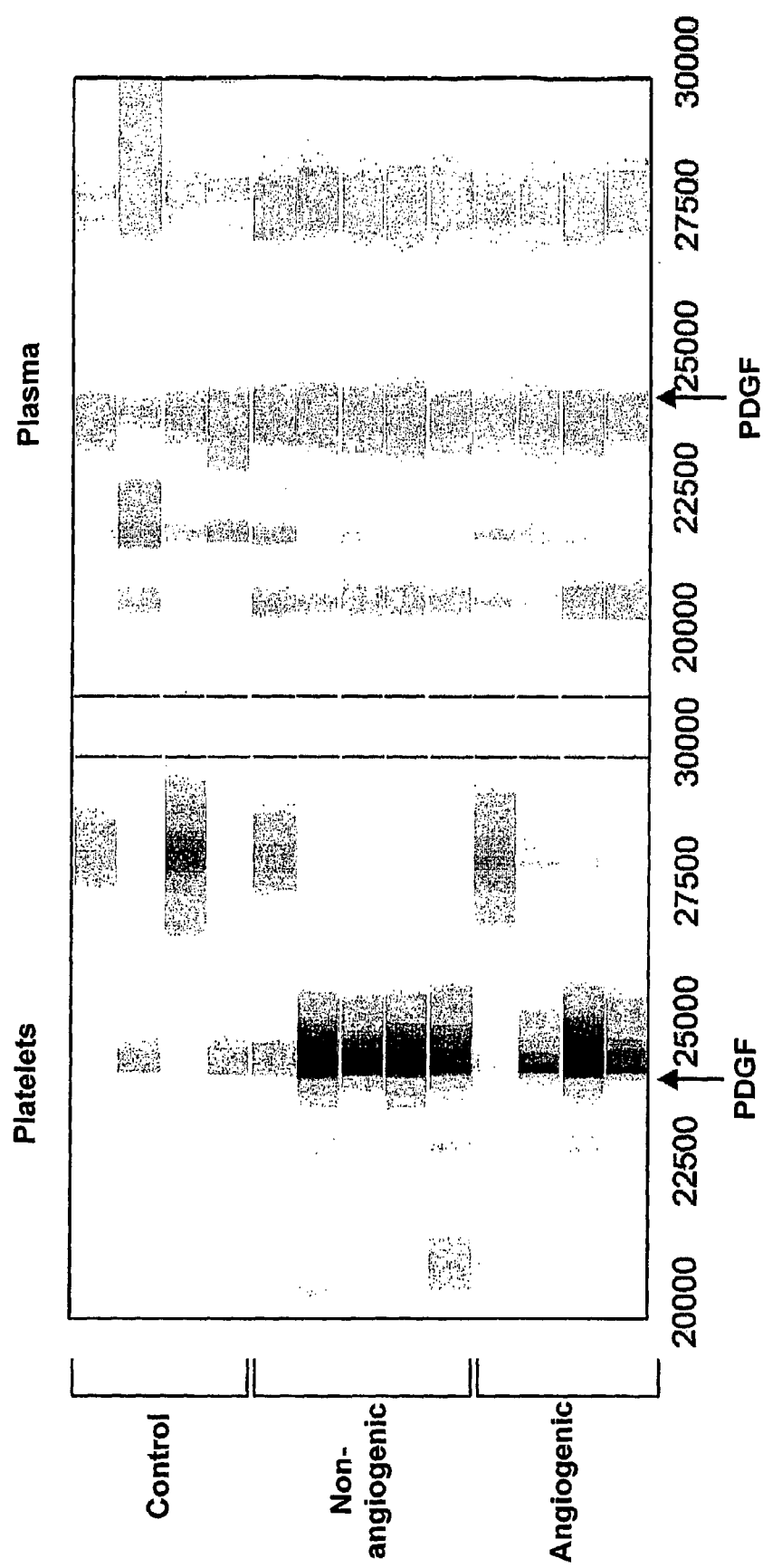
FIG. 4b shows an expression map showing PDGF levels in both platelet extracts and plasma.
Figure 5:
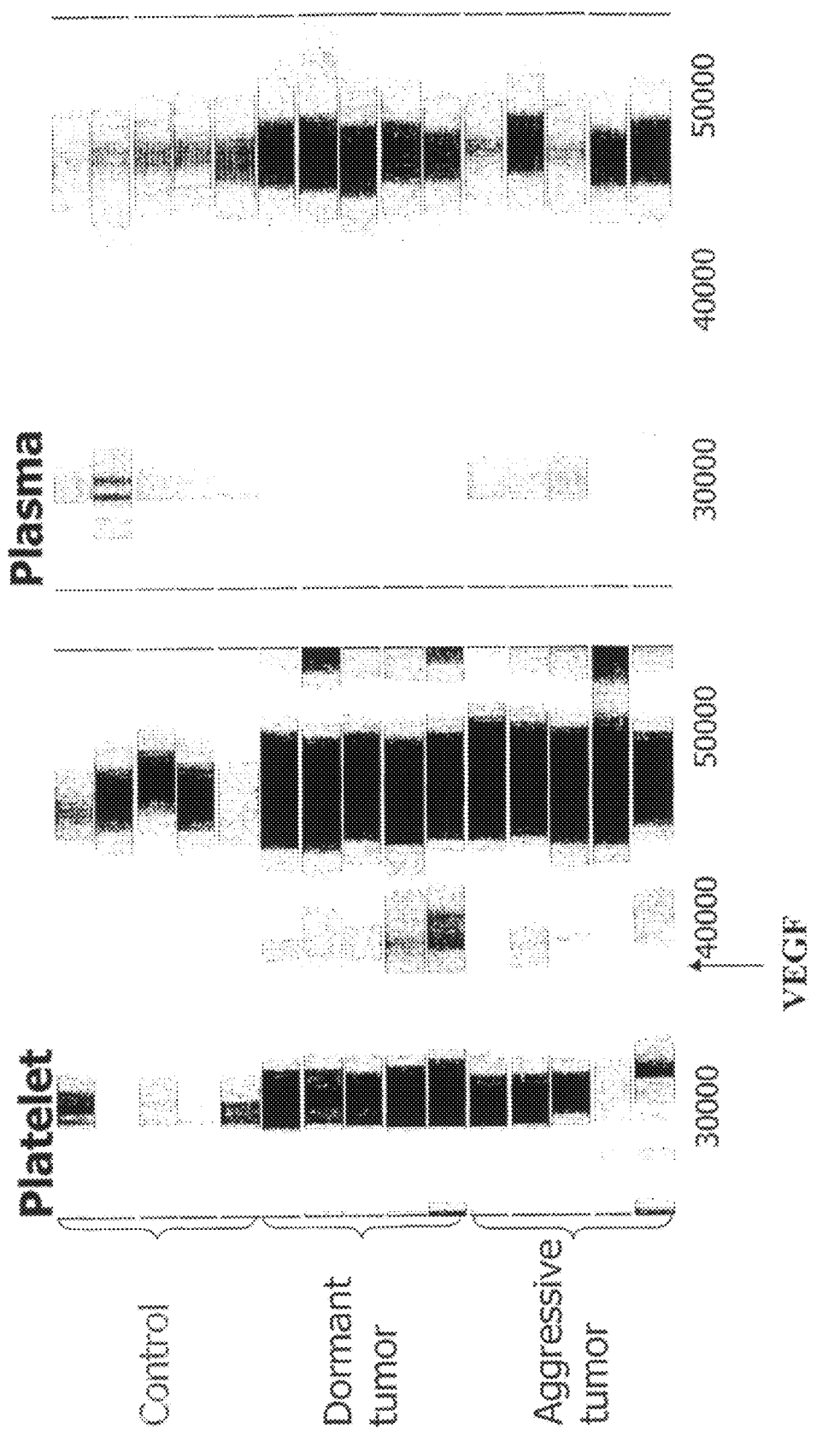
FIG. 5 shows an expression map of biomarkers observed following fractionation of platelet and plasma extracts on an anion exchange column, followed by profiling of one of those fractions (fraction 1) on a WCX2 PROTEINCHIP array. The figure shows that VEGF and fragments thereof are up-regulated in platelets from tumor-bearing mice (30 days after implantation), and shows that VEGF and its fragments are up-regulated to a greater extent in platelets from mice with aggressive (angiogenic) tumors as compared to mice with dormant tumors.
Figure 6:
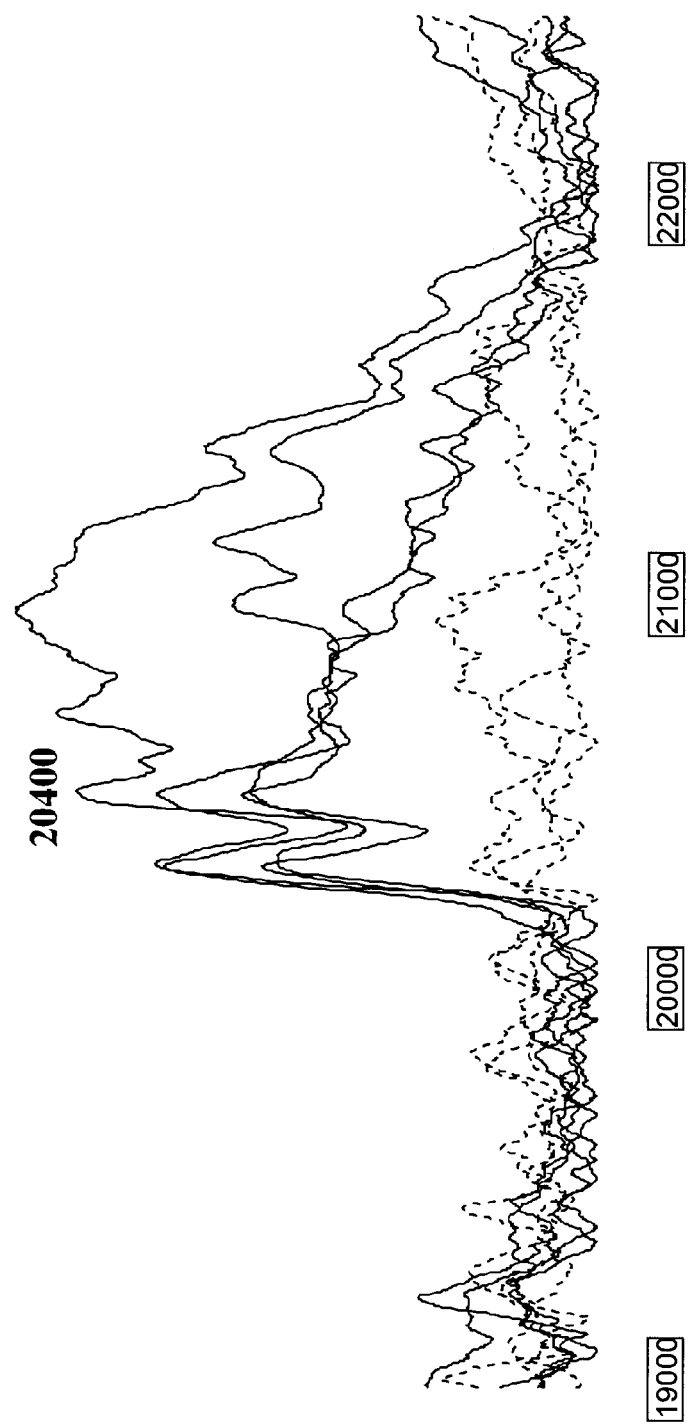
FIG. 6 shows an expression map of biomarkers observed after fractionation of platelet extracts on an anion exchange column, followed by profiling of one of those fractions (fraction 1) on a WCX2 PROTEINCHIP array. The figure shows that several markers, including a 20400 Da protein, are up-regulated in platelet extracts taken from tumor-bearing mice (black) compared to platelet extracts from control mice (dashed).
Figure 7:
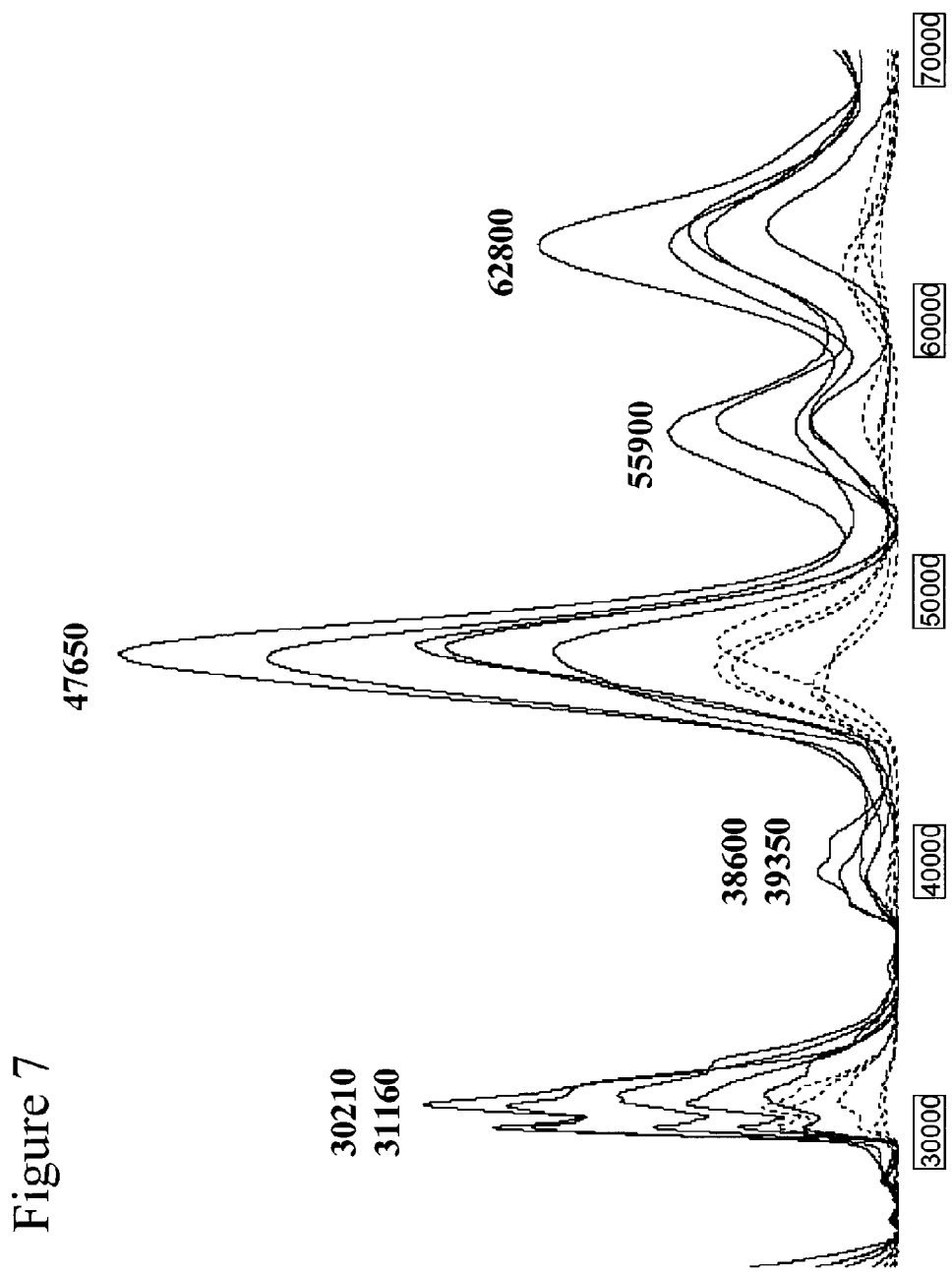
FIG. 7 shows an expression map of biomarkers observed after fractionation of platelet extracts on an anion exchange column, followed by profiling of one of those fractions (fraction 1) on a WCX2 PROTEINCHIP array. The figure indicates several markers that were identified to be up-regulated in dormant tumor-bearing mice (black) relative to control mice (dashed).
Figure 8:
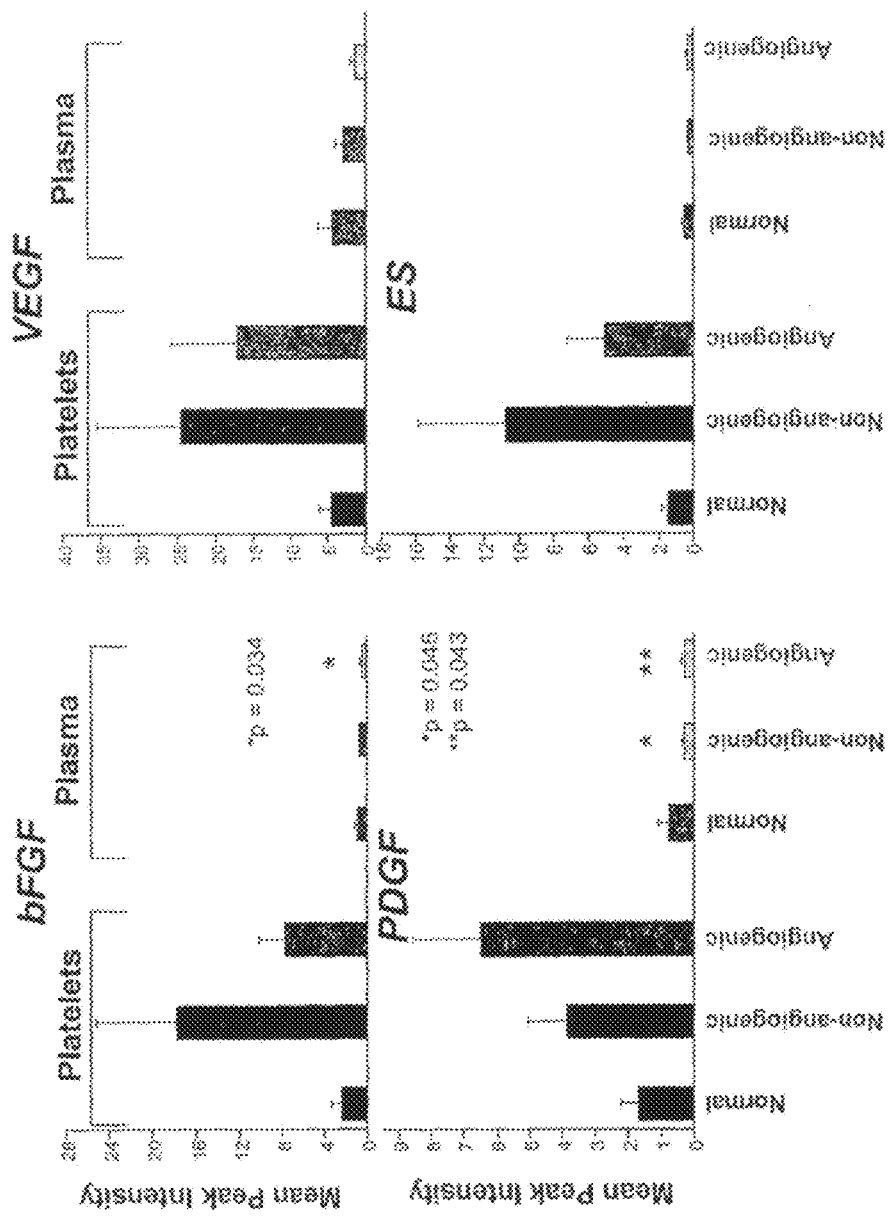
FIG. 8 shows plots of bFGF, VEGF, PDGF and endostatin levels in platelets and in plasma samples taken from normal, non-angiogenic and angiogenic tumor bearing mice.
Figure 9A:
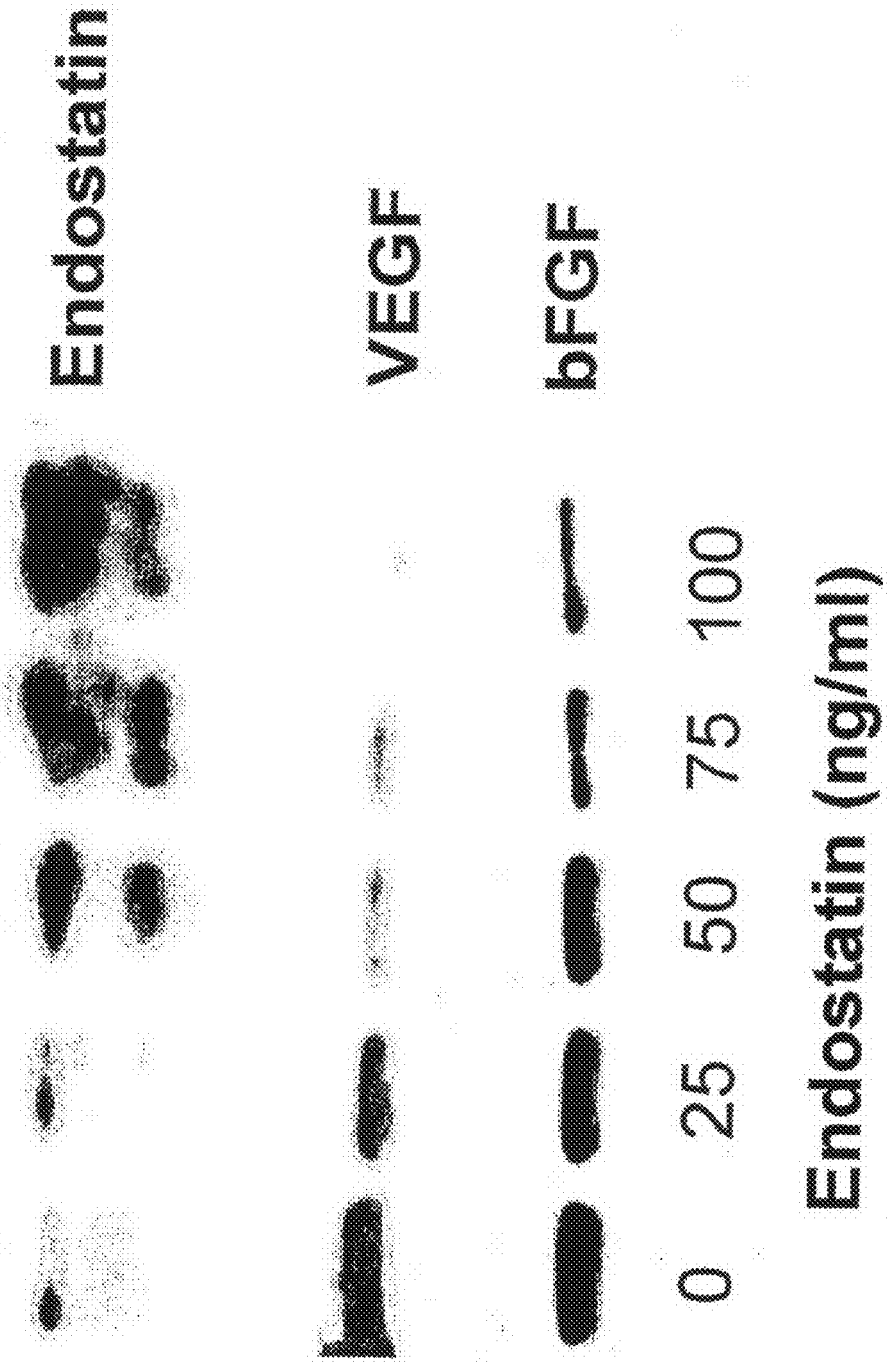
FIG. 9a shows a Western blot of platelet extracts, using anti-VEGF anti-bFGF, and anti-endostatin antibodies. Endostatin is shown to increase in platelets at the expense of VEGF and bFGF.
Figure 10:
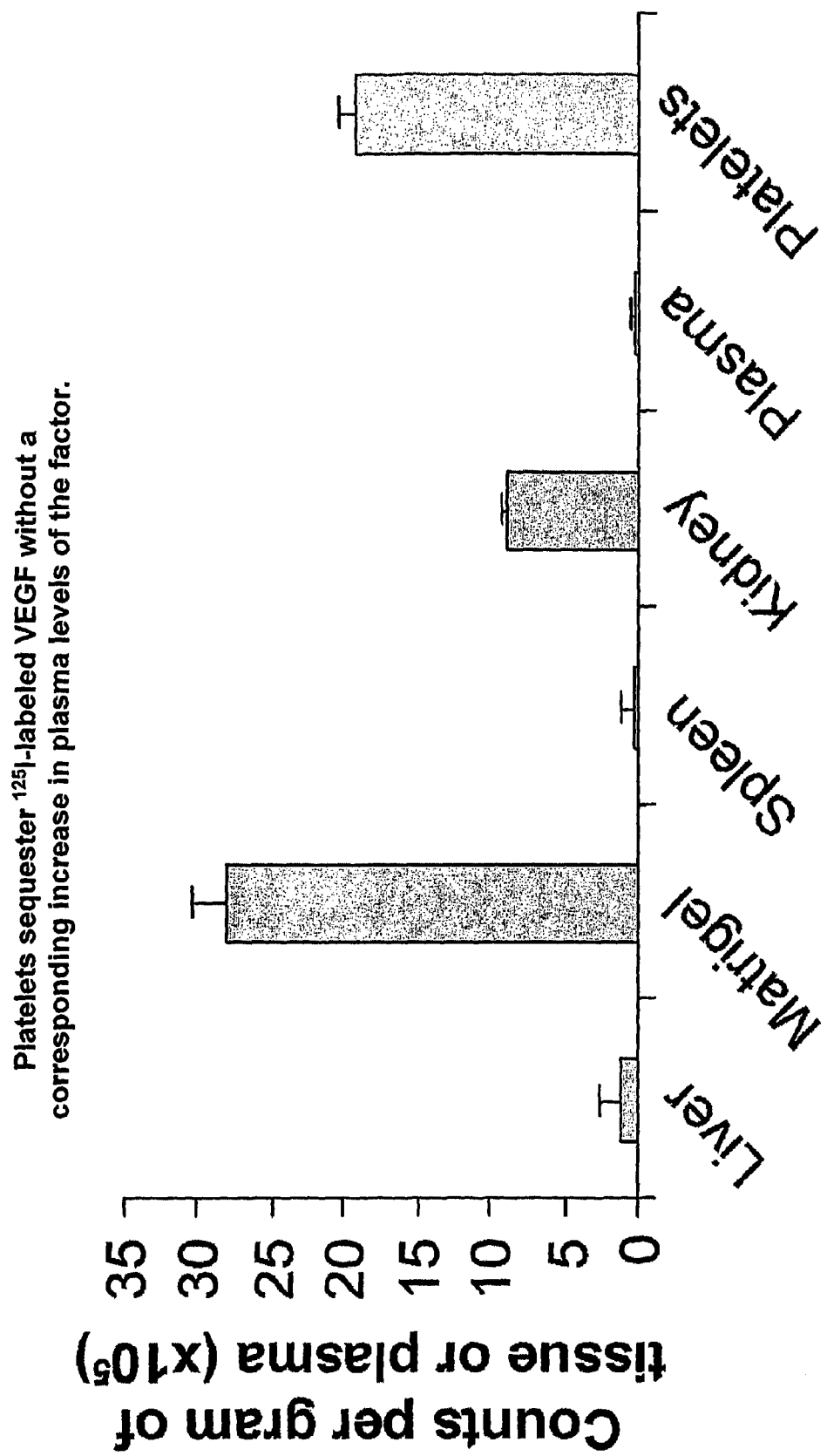
FIG. 10 shows the results of an experiment in which 100 microliters of MATRIGEL containing 50 ng of $^{125}$I-labeled VEGF was injected into a mouse. Various tissues were subsequently isolated from the mouse and the counts per gram of tissue were determined. The data show that platelets sequester $^{125}$I-labeled VEGF without a corresponding increase in plasma levels of the factor. Thus angiogenic regulatory proteins can be taken up by platelets in a selective and quantifiable manner even when a source as small as 100 microliter MATRIGEL pellet is implanted subcutaneously.
Figure 11:
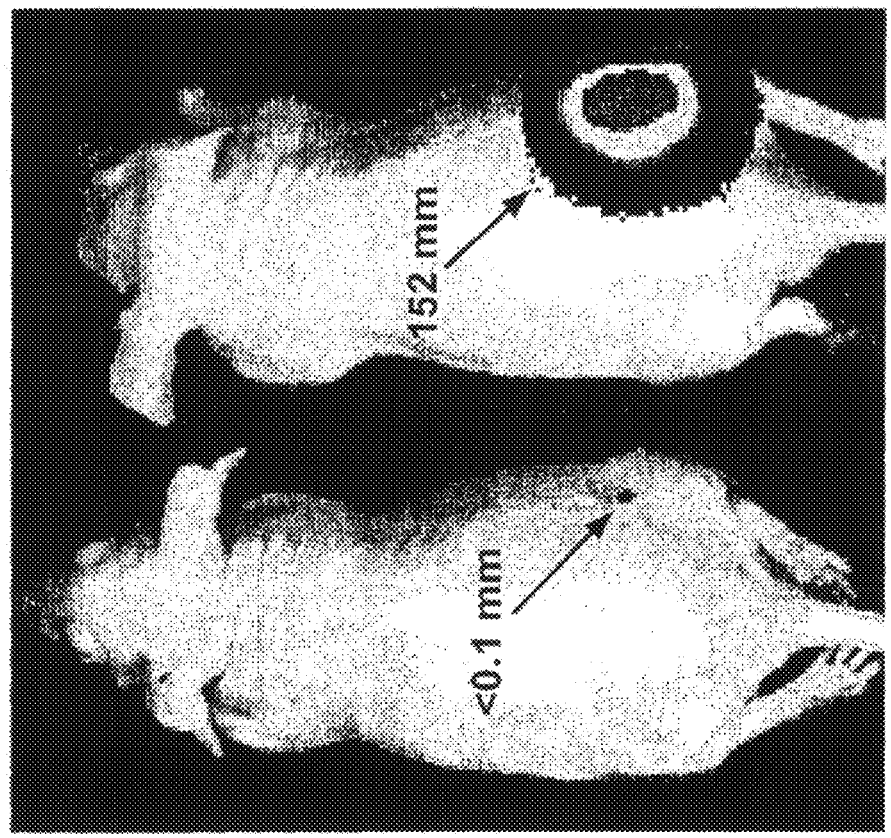
FIG. 11 shows the growth of non-angiogenic versus angiogenic human liposarcoma tumors in nude mice after 133 days of implantation.
Figure 12A:
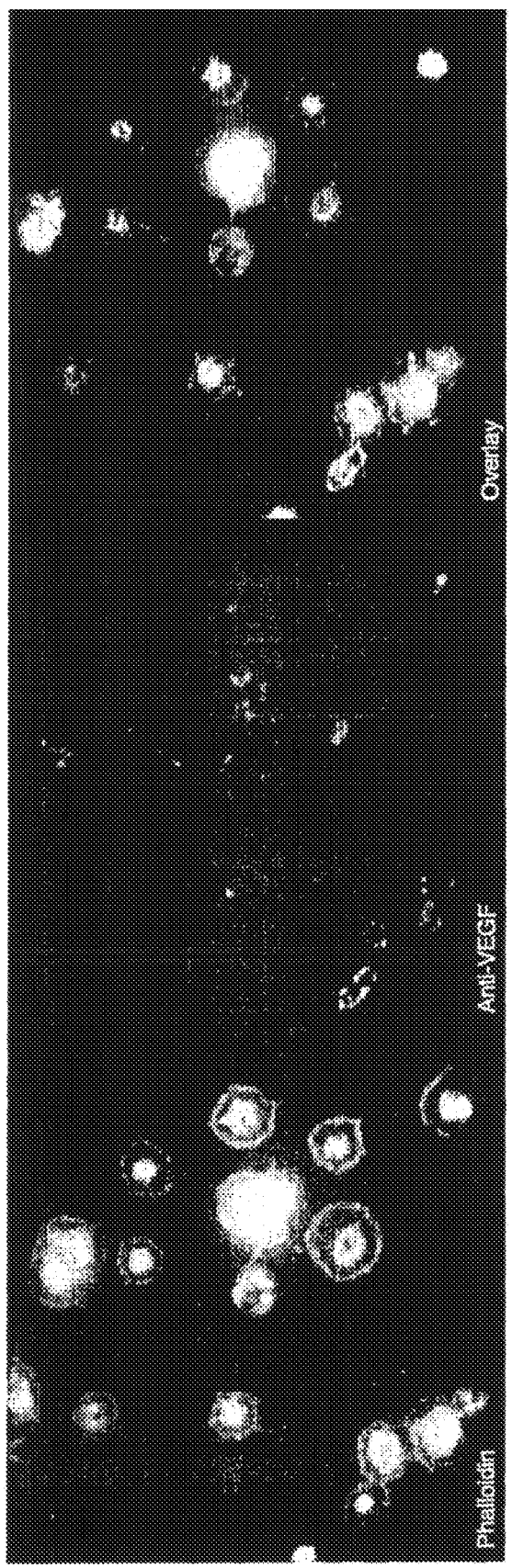
FIG. 12a-d show that the increased amounts in platelet extracts of angiogenic regulatory proteins such as VEGF represents a selective sequestration process and not a simple association with the platelet surface.
Figure 12B:
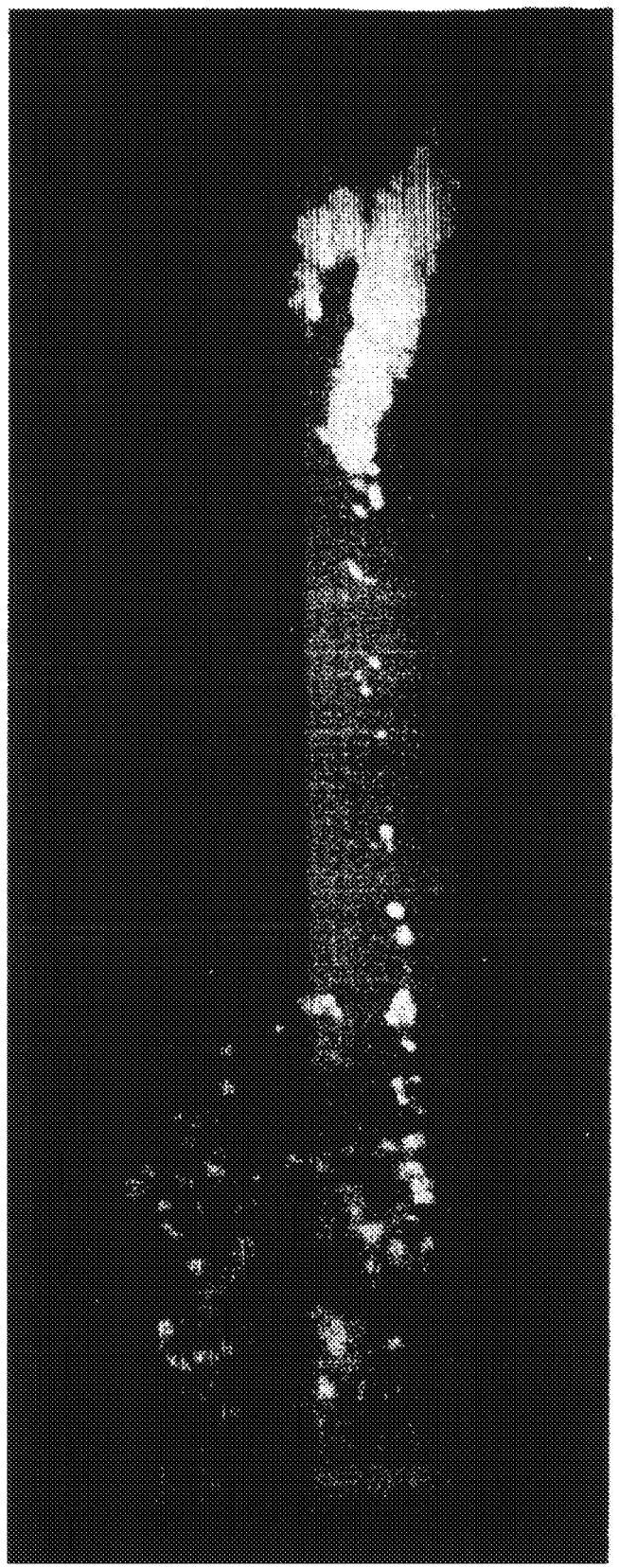
Figure 12C:
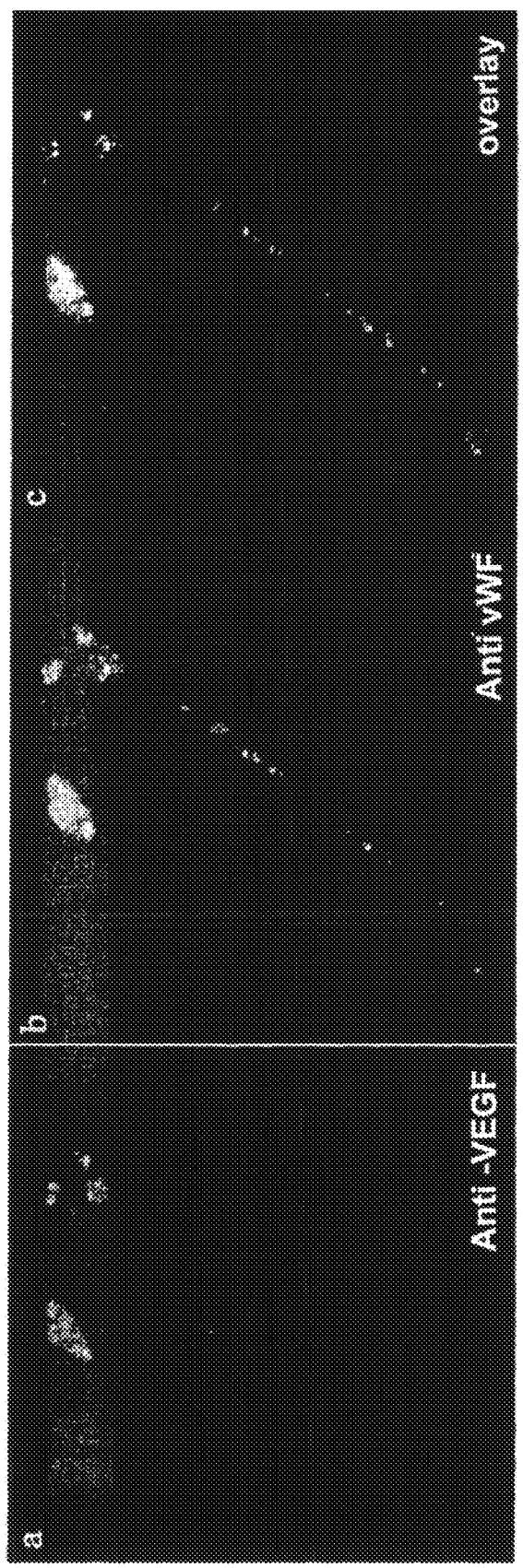
Figure 12D:
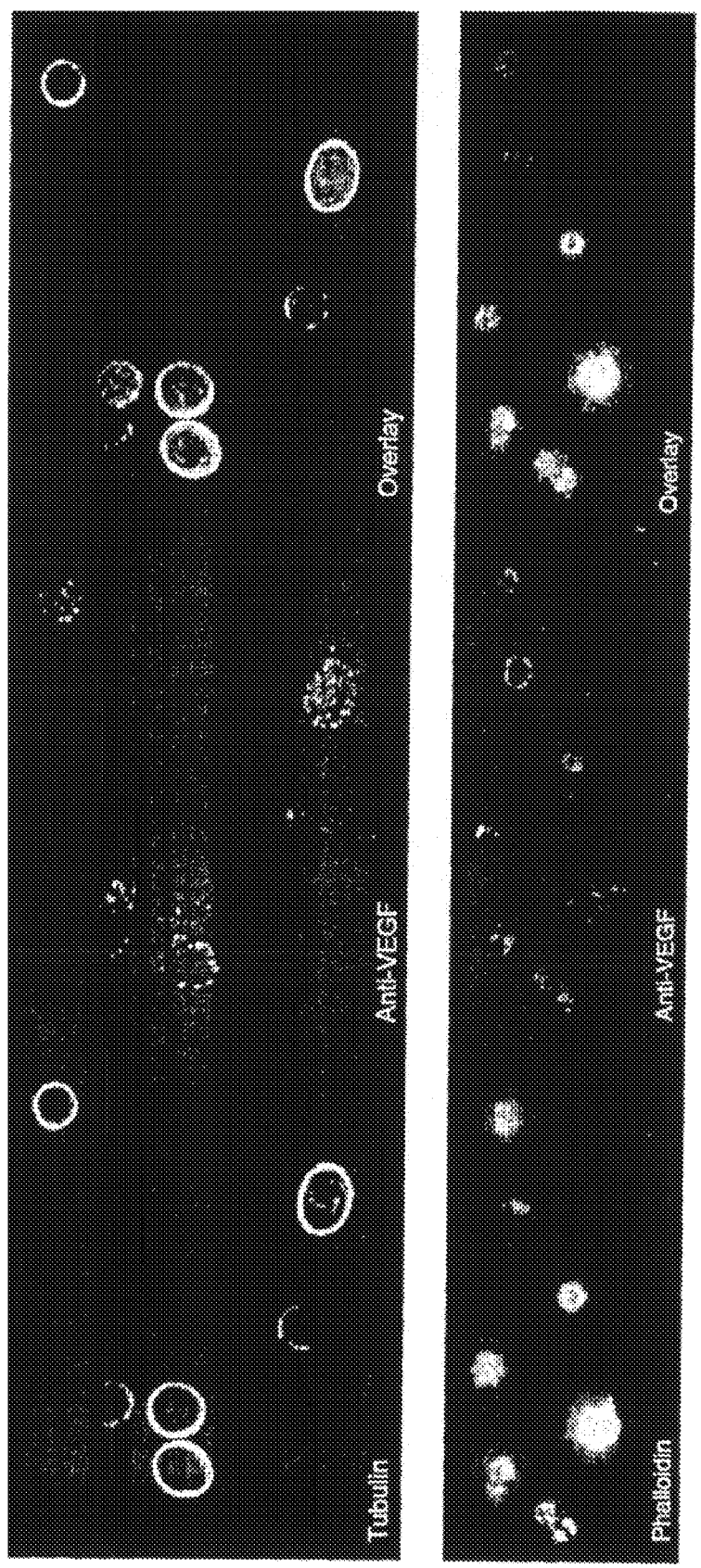

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

It has been found that platelets are a surprising good source of biomarkers for cancer and for other conditions characterized by differences in angiogenic (including anti-angiogenic) activity. In particular, platelet-derived biomarkers indicate changes in disease status very early, and can distinguish not only cancer from non-cancer, but benign tumors from malignant tumors. As such, the present invention provides a means for early diagnosis of clinical conditions as diverse as cancer, arthritis and pregnancy. Different clinical conditions may be distinguished using the present invention as each clinical condition may result in alteration of a different biomarker or cluster of multiple biomarkers. Thus the biomarker expression pattern for a given clinical condition may be a fingerprint or profile of a disease or metabolic state. Accordingly, the present invention provides kits, methods and devices for detecting and determining expression levels for biomarkers indicative of disease states or alterations in metabolic activity associated with a change in angiogenic activity.

The ability of the present invention to detect variations in tumor growth, for example, is illustrated in the Figures and Tables provided herein. The methods used for obtaining the data shown in the Figures and Tables are described in detail in the Examples. Briefly, mice were implanted with either dormant or aggressive tumors that were allowed to grow for a predetermined period of time. Control animals that were not implanted with a tumor were also surveyed. Platelets were obtained from these mice, homogenated, treated as described in the Examples, and analyzed using SELDI mass spectrometry and other methods practiced by those of ordinary skill in the art. Using this methodology, platelet-derived biomarkers have been identified that can indicate changes in disease status very early, and can distinguish not only cancer from non-cancer, but benign tumors from malignant tumors. For instance, as shown in the Figures and Table 1, the expression of the biomarker PF4 is enhanced in platelets from mice receiving tumors. Surprisingly, PF4 expression is highest in those mice receiving a dormant tumor implant. The Figures and Table 1 illustrate a similar result for the biomarker CTAP III, the dimer of which has a mass of approximately 16.2 kDa.

Note that only the molecular weight for a biomarker need be known to make the biomarker suitable for detection, although the shape and intensity of the peaks observed (e.g., FIG. 1a) and other parameters may also be used. For example, antibodies to the biomarker may be used or, if the activity of the biomarker is known, an enzyme assay could be used to detect and quantitate the biomarker.

II. Platelet Biomarkers for Cancerous and Non-Cancerous Tumors

Biomarkers

This invention provides polypeptide-based biomarkers that are differentially present in platelets of subjects having a condition characterized by angiogenic or anti-angiogenic activity, in particular, cancer versus normal (non-cancer) or benign (i.e., dormant) tumor versus malignancy. The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated, i.e., purified, form.

The biomarkers were discovered using SELDI technology employing PROTEINCHIP arrays from Ciphergen Biosystems, Inc. (Fremont, Calif.) ("Ciphergen"). Platelet samples were collected from murine subjects falling into one of three phenotypic statuses: normal, benign tumor, malignant tumor. The platelets were extracted with a urea buffer and then either applied directly to anion exchange, cation exchange or IMAC copper SELDI biochips for analysis, or fractionated on anion exchange beads and then applied to cation exchange SELDI biochips for analysis. Spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare the three different groups, and proteins were selected that differed significantly ($p<0.0001$) between the two groups. These methods are described in more detail in the Example Section.

The biomarkers thus discovered are presented in Table 1 and Table 2. The "PROTEINCHIP assay" column refers to the anion exchange chromatographic fraction in which the biomarker is found, the type of biochip to which the biomarker binds, and the wash conditions, as described in the Examples.

TABLE 1

| Marker | P-Value | Up or down regulated in tumor-bearing animals | PROTEINCHIP ® assay |
|---|---|---|---|
| 10.7, 34-39 kD vascular endothelial growth factor (VEGF) | <0.05 | Up | Fraction 1 and 2, WCX, wash with 50 mM Na acetate pH 5 Direct on IMAC30-Cu, wash with 50 mM TrisHCl, pH 7.5 |
| 20-25.7 kD platelet-derived growth factor (PDGF) | <0.05 | Up | Fraction 1 and 2, WCX, wash with 50 mM Na acetate pH 5 Direct on IMAC30-Cu, wash with 50 mM TrisHCl, pH 7.5 |
| 11, 14.7, 15, 16.5 kD fibroblast growth factor basic (bFGF) | <0.05 | Up | Fraction 1 and 2, WCX, wash with 50 mM Na acetate pH 5 Direct on IMAC30-Cu, wash with 50 mM TrisHCl, pH 7.5 |
| 8206 Da platelet factor 4 (PF4) | <0.01 | Up | Fraction 1 and 2, WCX, wash with 50 mM Na acetate pH 5 Direct on IMAC30-Cu, wash with 50 mM TrisHCl, pH 7.5 |

TABLE 1-continued

| Marker | P-Value | Up or down regulated in tumor-bearing animals | PROTEINCHIP ® assay |
|---|---|---|---|
| 8120 Da connective tissue activating protein III (CTAP III) | <0.01 | Up | Fraction 1 and 2, WCX, wash with 50 mM Na acetate pH 5 Direct on CM 10, wash with 50 mM TrisHCl pH 7.5 Direct on IMAC30-Cu, wash with 50 mM TrisHCl, pH 7.5 |
| 13.8, 20.3 kD Endostatin | <0.05 | Up | Fraction 1 and 2, WCX, wash with 50 mM Na acetate pH 5 Direct on IMAC30-Cu, wash with 50 mM TrisHCl, pH 7.5 |
| 13.8, 27.4 kD Tumstatin | <0.05 | Up | Fraction 1 and 2, WCX, wash with 50 mM Na acetate pH 5 Direct on IMAC30-Cu, wash with 50 mM TrisHCl, pH 7.5 |
| 13.6, 20.6, 23.9-24.7 kD Tissue inhibitor of metalloprotease | <0.05 | Up | Fraction 1 and 2, WCX, wash with 50 mM Na acetate pH 5 Direct on IMAC30-Cu, wash with 50 mM TrisHCl, pH 7.5 |
| 27.9 kD Apolipoprotein A I | <0.05 | Up | Fraction 1 and 2, WCX, wash with 50 mM Na acetate pH 5 Direct on IMAC30-Cu, wash with 50 mM TrisHCl, pH 7.5 Direct on Q10, wash with 50 mM TrisHCl, pH 7.5 |
| 8.7, 8.9 kD IL8 | <0.05 | Up | Fraction 1 and 2, WCX, wash with 50 mM Na acetate pH 5 |

TABLE 2

| | Marker | | | | P-Value | PROTEINCHIP ® assay |
|---|---|---|---|---|---|---|
| M: | 2019.1 | 2174.3 | 2373.6 | 2535.6 | <0.05 | Fractions 1 and 2, WCX chip, washed with 50 mM Na acetate pH 5 |
| | 2664.0 | 2755.2 | 2974.9 | 3392.5 | | |
| | 3696.1 | 3938.8 | 4204.2 | 4214.5 | | |
| | 4265.5 | 4367.4 | 4527.4 | 4905.7 | | |
| | 5023.5 | 5090.8 | 5166.5 | 5487.3 | | |
| | 5700.5 | 5836.7 | 5975.4 | 6050.2 | | |
| | 6106.5 | 6158.9 | 6258.4 | 6300.3 | | |
| | 6428.4 | 6481.2 | 6644.1 | 6715.2 | | |
| | 6837.7 | 6929.1 | 7084.9 | 7237.8 | | |
| | 7416.2 | 7489.7 | 7593.7 | 7649.3 | | |
| | 7684.5 | 7794.3 | 7856.7 | 7918.5 | | |
| | 7957.7 | 7992.1 | 8609.2 | 8680.6 | | |
| | 8724.4 | 8861.8 | 9061.8 | 9169.5 | | |
| | 9527.2 | 9950.2 | 10136.4 | 10843.1 | | |
| | 11180.6 | 11495.8 | 11637.5 | 11875.7 | | |
| | 12086.6 | 13610.6 | 13831.4 | 14710.8 | | |
| | 14861.9 | 15082.7 | 15303.2 | 15476.0 | | |
| | 15609.3 | 15720.8 | 15830.9 | 15917.9 | | |
| | 18025.1 | 18302.7 | 19612.6 | 20416.4 | | |
| | 20923.5 | 23211.1 | 23437.0 | 24077.2 | | |
| | 26646.9 | 30211.0 | 31160.1 | 36016.0 | | |
| | 38591.6 | 39346.3 | 46231.5 | 47675.7 | | |
| | 54408.5 | 55878.3 | 62830.5 | 71978.8 | | |
| | 78250.5 | 81455.9 | 94140.2 | | | |
| M: | 3855 | 3949.8 | 4034.4 | 4063.7 | <0.05 13 | Fraction 5, WCX chip, washed with 50 mM Na acetate pH 5 |
| | 4111.4 | 4148.7 | 4242.9 | 4263.8 | | |
| | 4389.4 | 4731.3 | 4751.6 | 5062.3 | | |
| | 5337.2 | 5733.7 | 5804.2 | 5843.4 | | |
| | 6537.4 | 6598.7 | 6671.2 | 6714.6 | | |
| | 6851.9 | 7154.8 | 7618.1 | 7627.8 | | |
| | 7709.2 | 7740.4 | 7948.2 | 8131.2 | | |
| | 8218.1 | 8337.4 | 8553.7 | 8594.0 | | |
| | 8671.4 | 8964.0 | 9103.3 | 9203.6 | | |
| | 9558.1 | 10885.5 | 11142.7 | 11208.2 | | |
| | 11250.6 | 11367.7 | 11532.5 | 14405.4 | | |
| | 15821.7 | 15936.4 | 16017.1 | 18618.5 | | |
| | 18980.2 | 19736.8 | 20346.0 | 23181.4 | | |
| | 23837.6 | 26536.7 | 27492.7 | 30154.2 | | |
| | 30991.6 | 31816.1 | 34901.2 | 39319.2 | | |
| | 41075.3 | 43369.4 | 45418.5 | 47235.7 | | |
| | 63928.6 | 78027.3 | 81611.9 | 90648.5 | | |

The biomarkers of this invention are characterized by their mass-to-charge ratio as determined by mass spectrometry. The mass-to-charge ratio ("M" value) of each biomarker is provided in Table 1 and Table 2 under the column heading "Marker." Thus, for example, M8206 has a measured mass-to-charge ratio of 8206. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by the shape of their spectral peak in time-of-flight mass spectrometry. Mass spectra showing peaks representing the biomarkers are presented in the Figures.

The biomarkers of this invention are further characterized by their binding properties on chromatographic surfaces. For example, markers found in Fraction III (pH 5 wash) are bound at pH 6 but elute with a wash at pH 5. Most of the biomarkers bind to cation exchange adsorbents (e.g., the Ciphergen® WCX PROTEINCHIP® array) after washing with 50 mM sodium acetate at pH 5, and many bind to IMAC biochips.

The identities of certain biomarkers of this invention have been determined, as indicated in Table 1. The method by which this determination was made is described in the Example Section. For biomarkers whose identify has been determined, the presence of the biomarker can be determined by other methods known in the art, including but not limited, to photometric and immunological detection.

As biomarkers detectable using the present invention may be characterized by mass-to-charge ratio, binding properties and spectral shape, they may be detected by mass spectrometry without prior knowledge of their specific identity. However, if desired, biomarkers whose identity has not been determined can be identified by, for example, determining the amino acid sequence of the polypeptides. For example, a protein biomarker may be identified by peptide-mapping with a number of enzymes, such as trypsin or V8 protease, and the molecular weights of the digestion fragments used to search databases for sequences that match the molecular weights of the digestion fragments generated by the proteases used in mapping. Alternatively, protein biomarkers may be sequenced using tandem mass spectrometry (MS) technology. In this method, the protein is isolated by, for example, gel electrophoresis. A band containing the biomarker is cut out and the protein subjected to protease digestion. Individual protein fragments are separated by the first mass spectrometer of the tandem MS. The fragment is then subjected to collision-induced cooling. This fragments the peptide producing a polypeptide ladder. The polypeptide ladder may then be analyzed by the second mass spectrometer of the tandem MS. Differences in mass of the members of the polypeptide ladder identifies the amino acids in the sequence. An entire protein may be sequenced this way, or a sequence fragment may be subjected to database mining to find identity candidates.

The preferred biological source for detection of the biomarkers is platelets.

The biomarkers of this invention are biomolecules. Accordingly, this invention provides these biomolecules in isolated form. The biomarkers can be isolated from biological fluids, such as platelet or serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

Use of Modified Forms of a Platelet-Associated Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention may also be used, themselves, as biomarkers. In certain cases, the modified forms may exhibit better discriminatory power in diagnosis than the specific forms set forth herein.

Modified forms of a biomarker can be initially detected by any methodology that can detect and distinguish the modified forms from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody derivatized bead-based technologies, such as xMAP technology of LUMINEX (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

In another aspect this invention provides a composition comprising a biospecific capture reagent, such as an antibody, bound to a biomarker of this invention. For example, an antibody that is directed against a biomarker of this invention and that is bound to the biomarker, is useful for detecting the biomarker. In one embodiment, the biospecific capture reagent is bound to a solid support, such as a bead, a chip, a membrane or a microtiter plate.

III. Detection of Platelet-Associated Biomarkers

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Prior to detection using the claimed invention, biomarkers may be fractionated to isolate them from other components of blood that may interfere with detection. Fractionation may include platelet isolation from other blood components, subcellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209; PCT International Publication No. WO 00/56934; and U.S. Pat. No. 5,242,828.

Detection by Mass Spectrometry

In a preferred embodiment, the biomarkers of this invention are detected by mass spectrometry, a method that employs a mass spectrometer to detect gas phase ions: Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

SELDI

A preferred mass spectrometric technique for use in the invention is "SurfaCe Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen PROTEINCHIP® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). Hydrophobic PROTEINCHIP arrays have isopropyl or nonylphenoxypoly(ethylene glycol)methacrylate functionalities. Anion exchange PROTEINCHIP arrays have quaternary ammonium functionalities. Cation exchange PROTEINCHIP arrays have carboxylate functionalities. Immobilized metal chelate PROTEINCHIP arrays have nitriloacetic acid functionalities that adsorb transition metal ions, such as copper, nickel, zinc, and gallium, by chelation. Preactivated PROTEINCHIP arrays have carboimidizole or epoxide functional groups that can react with groups on proteins for covalent binding.

Such biochips are further described in: U.S. Pat. No. 6,579, 719 (Hutchens and Yip, "Retentate Chromatography," Jun. 17, 2003); PCT International Publication No. WO 00/66265

(Rich et al., "Probes for a Gas Phase Ion Spectrometer,"Nov. 9, 2000); U.S. Pat. No. 6,555,813 (Beecher et al., "Sample Holder with Hydrophobic Coating for Gas Phase Mass Spectrometer," Apr. 29, 2003); U.S. Patent Application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application No. US 2003/0218130 A1 (Boschetti et al., "Biochips With Surfaces Coated With Polysaccharide-Based Hydrogels," Apr. 14, 2003) and U.S. Patent Application No. 60/448,467, entitled "Photocrosslinked Hydrogel Surface Coatings" (Huang et al., filed Feb. 21, 2003).

In general, a probe with an adsorbent surface is contacted with the sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's PROTEINCHIP® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's PROTEINCHIP® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

General Protocol for SELDI Detection of Platelet-Associated Biomarkers

As mentioned above, SELDI mass spectrometry is the preferred protocol contemplated by this invention for the detection of the biomarkers. The general protocol for detection of biomarkers using SELDI preferably begins with the sample containing the biomarkers being fractionated, thereby at least partially isolating the biomarker(s) of interest from the other components of the sample. Early fractionation of the sample is preferable as this approach frequently improves sensitivity of the claimed invention. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4, with fractions containing the biomarker being collected.

The sample to be tested (preferably pre-fractionated) is then contacted with an affinity probe comprising an cation exchange adsorbent (preferably a WCX PROTEINCHIP array (Ciphergen Biosystems, Inc.)) or an IMAC adsorbent (preferably an IMAC3 PROTEINCHIP array (Ciphergen Biosystems, Inc.)). The probe is then washed with a buffer that retains the biomarker while washing away unbound molecules. The biomarkers are detected by laser desorption/ionization mass spectrometry.

Alternatively, should antibodies that recognize the biomarker be available, as is the case with PF4 and CTAP III, a biospecific probe may be constructed. Such a probe may be formed by contacting the antibodies to the surface of a functionalized probe such as a pre-activated PS10 or PS20 PROTEINCHIP array (Ciphergen Biosystems, Inc.). Once attached to the surface of the probe, the probe may then be used to capture biomarkers from a sample onto the probe surface. The biomarkers then may be detected by, e.g., laser desorption/ionization mass spectrometry.

Detection by Immunoassay

In another embodiment, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated PROTEINCHIP array. The biomarker is then specifically captured on the biochip through this reagent, and the captured biomarker is detected by mass spectrometry.

IV. Correlating Changes in Biomarker Expression to Angiogenic Status

Use of the present invention allows the practitioner to diagnose changes in the metabolic state of an individual associated with increased angiogenic activity. This is accomplished by monitoring changes in expression levels of platelet-associated biomarkers resulting from the angiogenic activity associated with the altered metabolic state sought to be detected. Accordingly, preferred biomarkers of the present invention are associated with angiogenesis or angiostasis, although precise identification of suitable biomarkers is not a prerequisite to practicing the claimed invention using those biomarkers. Practice of the claimed invention in the manner described may be performed with a single detectable marker or multiple detectable markers that individually or as a group display altered expression levels in response to modifications of angiogenic activity associated with a physiological modification such as a cancer, infection, pregnancy, tissue injury and the like.

Biomarker expression may be monitored in a variety of ways. For example, a single sample may be analyzed for biomarker expression levels that are subsequently compared to a control threshold determined from sampling a representative control population. Alternatively multiple samples from a single patient taken over a time course may be compared to determine whether biomarker expression levels are increasing or decreasing. This approach is particularly useful when evaluating the prognosis of a patient after treatment for a disease that affects biomarker expression. Still other biomarker evaluations will be readily apparent to one of skill in the art, who may perform the analysis without undue experimentation.

Single Markers

Detection of individual biomarkers is contemplated for the claim invention, provided the biomarker meets the criteria noted above, particularly correlation with the disease or change in metabolic state sought to be detected through use of the invention. Single biomarkers may be used in diagnostic tests to assess angiogenic status in a subject, e.g., to diagnose the presence of cancer or alterations in the course of a disease, such as certain cancers, which affect angiogenic activity in a patient. The phrase "angiogenic status" includes distinguishing, inter alia, disease v. non-disease states and, in particular, aggressive cancer v. dormant cancer or aggressive cancer v. non-cancer. In addition, angiogenic status may include cancers of various types. Based on this status, further procedures may be indicated, including additional diagnostic tests or therapeutic procedures or regimens.

Each biomarker listed in Table 1 and Table 2 is differentially expressed in response to an alteration in angiogenesis in a patient. Therefore, each of these biomarkers is individually useful in aiding in the determination of angiogenic status. Some embodiments of the present invention involve, for example, measuring the expression level of the selected biomarker in a platelet preparation. By comparing the expression level of the biomarker with an earlier-determined expression level in the same individual, one of skill in the art may determine the course of disease, or response of the disease to treatment. Alternatively, the expression level of the detected biomarker may be compared to threshold values for one or more disease states, e.g., as determined by surveying populations of individuals displaying suitable known phenotypes. Exemplary known biomarkers that may be suitable for diagnostic or prognostic purposes by detection individually with the present invention include, but are not limited to, VEGF, PDGF, bFGF PF4, CTAPIII, endostatin, tumstatin, tissue inhibitor of metalloprotease, apolipoprotein A., IL8, TGF, NGAL, MIP, metalloproteases, BDNF, NGF, CTGF, angiogenin, angiopoietins, angiostatin, and thrombospondin.

Use of individual biomarkers as indicators of alterations in angiogenic activity typically involves detecting the biomarker, followed by correlation of the determined biomarker expression level with threshold levels associated with a particular disease or change in metabolic state. For example, capture on a SELDI biochip followed by detection by mass spectrometry and, second, comparing the measurement with a diagnostic amount or cut-off that distinguishes a positive angiogenic status from a negative angiogenic status. The diagnostic amount represents a measured amount of a biomarker above or below which a subject is classified as having a particular angiogenic status. For example, if the biomarker is up-regulated compared to normal during tumor formation, then a measured amount above the diagnostic cut-off provides a diagnosis of cancer. Alternatively, if the biomarker is down-regulated during treatment of an aggressive tumor, then a measured amount below the diagnostic cut-off provides a diagnosis of tumor regression, or passage of the tumor to a dormant state.

The measured level of a biomarker may also be used to facilitate the diagnosis of particular types of cancers or to distinguish between different cancer types. For example, if a biomarker or combination of biomarkers is up-regulated above a particular level in certain types of cancers compared to others, a measured amount of the biomarker above the diagnostic cut-off provides an indication that a particular type of cancer is present. Furthermore, combinations of biomarkers may be used to provide additional diagnostic information, as described below. Some examples of types of cancers which may be identified and distinguished from each other using the biomarkers and techniques described herein include breast cancer, liver cancer, lung cancer, hemangioblastomas, neuroblastomas, bladder cancer, prostate cancer, gastric cancer, cancers of the brain, and colon cancer. Carcinomas, sarcomas, leukemia, lymphoma and myolomas may also be distinguished using the biomarkers and methods described herein. Furthermore, different cancer types express different patterns of biomarkers and are distinguished from each other thereby. The patterns characteristic of each cancer type can be determined as described herein by, e.g., analyzing samples from each cancer type with a learning algorithm to generate a classification algorithm that can classify a sample based on cancer type.

As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different angiogenic statuses, as was done here, and drawing the cut-off to suit the diagnostician's desired levels of specificity and sensitivity.

Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. In the context of the present invention, at least two, preferably 3, 4, 5, 6 or 7, more preferably 10, 15 or 20 different biomarker expression levels are determined in the diagnosis of a disease or change in metabolic state. Exemplary biomarkers that may be used in combination include PF4, VEGF, PDGF, bFGF, PDECGF, CTGF, angiogenin, angiopoietins, angiostatin, endostatin, and thrombospondin. A preferred embodiment of the present invention detects a plurality of biomarkers including bFGF and at least one other biomarker selected from the group consisting of VEGF, PDGF, PDECGF, CTGF, angiogenin, angiopoietins, PF4, angiostatin, endostatin, and thrombospondin. An alternative preferred embodiment detects a plurality of biomarkers including PF4 and at least one other biomarker selected from the group consisting of VEGF, PDGF, bFGF, PDECGF, CTGF, angiogenin, angiopoietins, angiostatin, endostatin, and thrombospondin.

V. Generation of Classification Algorithms for Qualifying Tumor Status

As discussed above, analysis of detected biomarker expression levels may be performed manually or automated using computer software. Single sample analysis may be performed, or multiple sample analysis may be undertaken, with each of the multiple samples being taken from the individual under study at an appropriate time during the course of treatment or evaluation. Accuracy of analysis is particularly important as the determination may be used for both monitoring progress during treatment of a disease or change in metabolic state, and for diagnosing the disease or change in metabolic state. In preferred embodiments of the claimed invention, managing patient treatment is based on categorizing expression levels to accurately reflect the disease or metabolic status of the patient under evaluation.

Many different categorization strategies suitable for use with the present invention are known in the art. A preferable strategy identifies distinct expression levels of a biomarker with distinct stages of disease progression. For example, in tumor growth, the tumor may go through a series of stages from nascent formation to metastasis. Thus a suitable categorization scheme may include "aggressive" characterized by tumor growth and/or metastatic activity; dormant, to identify tumors that are not growing or actively metastasizing; regressive, to identify a tumor that is shrinking, for example after chemotherapy; and no tumor.

In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for determining angiogenic status. The classification algorithms, in turn, form the base for diagnostic tests by providing diagnostic values (e.g., cut-off points) for biomarkers used singly or in combination.

VI. Managing Patient Care

In providing methods kits and devices for the diagnosis and evaluation of prognosis for disease states, the present invention has utility in providing tools for management of patient care. In particular, the present invention finds use in diagnosing and evaluating the treatment of a variety of diseases that lead to a change in angiogenic activity in the patient. Such conditions may include, for example, cancer, pregnancy, infection (e.g., hepatitis), injury, and arthritic conditions. In certain embodiments of the present invention, methods of qualifying angiogenic status, the methods further comprise managing subject treatment based on the status. Such management includes the actions of the physician or clinician subsequent to determining disease status. For example, if a physician makes a diagnosis of aggressive cancer, then a certain regime of treatment, such as chemotherapy or surgery might follow. Alternatively, a diagnosis of no tumor or dormant tumor might be followed with further testing to determine a specific disease afflicting the patient.

A particularly useful aspect of the present invention is that it provides for early detection of potentially life-threatening conditions, as noted above. Early diagnosis enhances the prognosis for recovery by allowing early treatment of the condition. By way of example, early detection of cancer allows for earlier and less debilitating chemotherapy or surgical removal of any tumor prior to metastasis. Early detection of arthritis allows for drug intervention to control inflammation before debilitating joint injury occurs, slowing the symptoms of the disease.

In one embodiment, this invention provides methods for determining the course of cancer progression or cancer regression in a subject. Over time, the amounts or relative amounts (e.g., the pattern) of the biomarkers changes. For example, the tumstatin biomarkers in Table 1 are increased during angiogenesis. Therefore, the trend of this biomarkers, e.g., increasing over time, indicates that angiogenesis in the subject is increasing. Likewise, decreasing levels of tumstatin indicate that angiogenesis in the subject is decreasing. Accordingly, this method involves measuring one or more biomarkers in a subject at least two different time points, e.g., a first time and a second time, and comparing the change in amounts, if any. The course of disease, e.g., cancer progression or regression, is determined based on these comparisons.

After diagnosis, detecting biomarkers using the present invention allows evaluation of the effectiveness of the treatment regime being employed. For example, in cancers, detecting a decrease in expression of the CTAP III biomarker after treatment of a dormant tumor correlates with the tumor altering phenotype to an aggressive tumor. Conversely, detecting a subsequent increase in CTAP III correlates with a change in the tumor phenotype from aggressive to dormant or absent.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of a biomarker indicative of a disease or metabolic state is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

VII. Kits for Detection of Platelet-Associated Biomarkers for Cancerous and Non-Cancerous Tumors In another aspect, the present invention provides kits for qualifying disease status or a change in metabolic activity associated with angiogenesis. These kits are used to detect biomarkers according to the invention. In one embodiment, the kit comprises a solid support, such as a chip, a microtiter plate or a bead or resin having a adsorbent attached thereon, wherein the adsorbent binds a biomarker of the invention. Thus, for example, the kits of the present invention may comprise mass spectrometry probes for SELDI, such as PROTEINCHIP® arrays. In the case of biospecfic adsorbents, the kit may comprise a solid support with a reactive surface, and a container comprising the biospecific adsorbent. In some embodiments, the solid support is coupled to one or more adsorbents capable of binding at least one, preferably at least 2, 3 or 4 biomarkers such as those set forth in Table 1 and Table 2. In preferred embodiments, the biomarkers may be PF4, VEGF, PDGF, bFGF, PDECGF, CTGF, angiogenin, angiopoietins, angiostatin, endostatin or thrombospondin and combinations thereof. Preferable absorbents for coupling to the solid support include cation and anion exchange, hydrophobic and biospecific adsorbents. Preferred biospecific adsorbents include antibodies, aptamers, complementary nucleic acids, Affibodies, and the like. Additional biospecific adsorbents will be readily recognized by one of skill in the art.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

VIII. Diagnostic Systems

The present invention also contemplates diagnostic systems for detecting biomarkers whose expression is altered in response to changes in angiogenic activity in a patient. The diagnostic systems of the invention are preferably operated in a single step, but are not limited to such. For example, some embodiments comprise a plurality of adsorbent surfaces binding a plurality of platelet-associated biomarkers. Preferably, the adsorbents are biospecific adsorbents that specifically adsorb the biomarkers of interest. The diagnostic systems of the invention also have a means for detecting the biomarkers of interest, which may be a mass spectrometer.

By way of example, a preferred embodiment of the present invention accepts a plasma homogenate on a sintered frit. The frit is in fluid communication with a bibulous material capable of supporting capillary flow of a liquid. Within the bibulous material are reagents, including a fluidly mobile biospecific adsorbent that specifically recognizes the biomarker to be detected. Preferably, the fluidly mobile biospecific adsorbent includes a detectable label, more preferably, a visible label. Further downstream in the bibulous material is a fixed biospecific adsorbent recognizing the biomarker to be detected.

Using a simple device, such as that described above, a plasma homogenate introduced to the sintered frit is filtered free of cellular debris. The remaining liquid progresses to the bibulous material, which wicks the liquid into and ultimately along its length. In traversing the bibulous material, the fluidly mobile biospecific adsorbent is solublized and binds to the biomarker to be detected forming a complex. As the liquid progresses further through the bibulous material, the complex encounters and binds to the fixed biospecific adsorbent. As the complex binds to the fixed biospecific adsorbent, it becomes concentrated at the point where the fixed biospecific adsorbent is attached to the bibulous material, where it may be detected. The device may optionally be washed with a wash buffer after complex binding to remove potentially interfering material present in the original homogenate.

One of skill in the art will readily recognize that there are several variant device formats that perform in substantially the same manner as the preferred device described above. For example, the device could essentially be performed in an ELISA-type manner using biospecific reagents coupled to the floor of microtitre plate wells. In this format, the homogenate is added to a well. Excess homogenate is then removed and the well washed with a wash buffer. Finally, the labeled mobile antibody is added and the resulting complex detected.

One of skill in the art will readily recognize the format of the device described above as being well known, with many variants falling within the scope of the present invention. For example, similar devices are described in U.S. Pat. Nos. 5,409,664, 6,146,589, 4,960,691, 5,260,193, 5,202,268 and 5,766,961.

IX. Use of Biomarkers for Cancer in Screening Assays and Methods of Treating Cancer The methods of the present invention have other applications as well. For example, the biomarkers can be used to screen for compounds that modulate the expression of the biomarkers in vitro or in vivo, which compounds in turn may be useful in treating or preventing cancer in patients or in treating or preventing the transformation of a tumor from a dormant tumor to an aggressive tumor. In another example, the biomarkers can be used to monitor the response to treatments for cancer. In yet another example, the biomarkers can be used in heredity studies to determine if the subject is at risk for developing cancer.

Thus, for example, the kits of this invention could include a solid substrate having a hydrophobic function, such as a protein biochip (e.g., a Ciphergen H50 PROTEINCHIP array, e.g., PROTEINCHIP array) and a sodium acetate buffer for washing the substrate, as well as instructions providing a protocol to measure the platelet-associated biomarkers of this invention on the chip and to use these measurements to diagnose, for example, cancer.

Compounds suitable for therapeutic testing may be screened initially by identifying compounds which interact with one or more biomarkers listed in Table 1 and Table 2. By way of example, screening might include recombinantly expressing a biomarker listed in Table 1 or Table 2, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table 1 or Table 2, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of Table 1 or Table 2 may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table 1 or Table 2 may also be measured. For example, the self-assembly of a multi-protein complex which includes one of the biomarkers of Table 1 and Table 2 may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table 1 or Table 2 may be administered to patients who are suffering from or are at risk of developing cancer. For example, the administration of a test compound which increases the activity of a particular biomarker may decrease the risk of cancer in a patient if the activity of the particular biomarker in vivo prevents the accumulation of proteins for cancer. Conversely, the administration of a test compound which decreases the activity of a particular biomarker may decrease the risk of cancer in a patient if the increased activity of the biomarker is responsible, at least in part, for the onset of cancer.

In an additional aspect, the invention provides a method for identifying compounds useful for the treatment of disorders such as cancer which are associated with increased levels of modified forms of the platelet-associated biomarkers of Table 1 and Table 2. For example, in one embodiment, cell extracts or expression libraries may be screened for compounds which catalyze the cleavage of the full-length biomarkers to form truncated forms. In one embodiment of such a screening assay, cleavage of the biomarkers may be detected by attaching a fluorophore to the biomarker which remains quenched when biomarker is uncleaved but which fluoresces when the biomarker is cleaved. Alternatively, a version of full-length biomarker modified so as to render the amide bond between certain amino acids uncleavable may be used to selectively bind or "trap" the cellular protesase which cleaves the full-length biomarker at that site in vivo. Methods for screening and identifying proteases and their targets are well-documented in the scientific literature, e.g., in Lopez-Ottin et al. (Nature Reviews, 3:509-519 (2002)).

In another embodiment, this invention provides methods for determining the therapeutic efficacy of a pharmaceutical drug, e.g., an anti-angiogenic or anti-tumorigenic compound. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, the PF4 and CTAP III biomarkers in Table I increase in platelets from tumor-bearing subjects. Therefore, one can follow the course of the amounts of these biomarkers in the subject during the course of treating a tumor. Accordingly, this method involves measuring one or more biomarkers in a subject receiving drug therapy, and correlating the amounts of the biomarkers with the disease status of the subject. One embodiment of this method involves determining the levels of the biomarkers at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

In yet another embodiment, the invention provides a method for treating or reducing the progression or likelihood of a disease, e.g., cancer, which is associated with the increased levels of a truncated biomarker. For example, after one or more proteins have been identified which cleave a full-length biomarker of Table 1 or 2, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of the platelet-associated biomarker.

At the clinical level, screening a test compound includes obtaining samples from test subjects before and after the subjects have been exposed to a test compound. The levels in the samples of one or more of the platelet-associated biomarkers listed in Table 1 and Table 2 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table 1 and Table 2 may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table 1 and Table 2 may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with cancer, test compounds will be screened for their ability to slow or stop the progression of the cancer within the spirit and purview of this application and scope of the appended claims. All publication.

X. EXAMPLES

Example 1

Identification of Biomarkers for Cancer

A. Sample Preparation:

Blood was collected from anesthetized mice by direct cardiac puncture into 3.2% sodium citrate polyethylene tube and spun as soon as possible at 200 g. Upper phase, platelet rich plasma (PRP), was then transferred into a fresh tube, and platelets (P) separated by centrifugation at 800 g. The isolated platelet pellet (P) and platelet poor plasma (PPP) supernatant were analyzed separately.

Platelets pellets (P) from each mouse were extracted with 9M urea, 2% CHAPS (3-[(3-Cholamidopropyl)dimethylammonio]-1-propansulfonat), 50 mM TrisHCl, pH 9; centrifuged at 10,000×g at 4° C. for 1 min, and platelet extract fractionated as described below. 20 µl of PPP from each mouse was denatured with 40 µl of U9 buffer (9M urea, 2% CHAPS, 50 mM TrisHCl, pH 9), and the pure plasma extract fractionated as described below. Tumor tissue from each mouse was also extracted with U9 buffer by grinding the tissue with a disposable pestle and vortexing for 15 min at 4° C. Extracted proteins were harvested by centrifugation at 10,000×g at 4° C. for 10 min. Pure tumor extracts were then fractionated as described below.

B. Sample Fractionation:

Tumor, platelet pellet and plasma samples were fractionated by anion-exchange chromatography modified after the EDM Serum Fractionation protocol (Ciphergen®, Fremont, Calif.). The fractionation was performed in a 96-well format filter plate on a Beckman Biomek® 2000 Laboratory Work Station equipped with a DPC® Micromix 5 shaker. An aliquot of 20 µl of the platelet and tumor extract, and 60 µl of denatured plasma diluted with 100 ul of 50 mM TrisHCl pH9 and was transferred to a filter bottom 96-well microplate pre-filled with BioSepra Q Ceramic HyperD® F sorbent beads rehydrated with 50 mM TrisHCl, pH 9, and pre-equilibrated with 50 mM Tris-HCl, pH 9.0. All liquids were removed from the filtration plate using a multiscreen vacuum manifold (Millipore, Bedford, Mass.). After incubating for 30 min at 4° C., the flow-through was collected as Fraction I. The filtration plate was incubated with 2×100 µl of the following buffers to yield the following fractions: 1M urea, 0.1% CHAPS, 50 mM NaCl, 2.5% acetonitrile, 50 mM TrisHCl pH 7.5 (Fraction II), 1M urea, 0.1% CHAPS, 50 mM NaCl, 2.5% acetonitrile 50 mM NaAcetate, pH 5.0 (Fraction III), 1M urea, 0.1% CHAPS, 50 mM NaCl, 2.5% acetonitrile 50 mM NaAcetate, pH 4.0 (Fraction IV), 1M urea, 0.1% CHAPS, 500 mM NaCl, 2.5% acetonitrile 50 mM NaCitrate, pH 3.0 (Fraction V), and 33.3% isopropanol/16.7% acetonitrile/8% formic acid (Fraction VI). These are the fractions referred to in Tables I and Tables II.

C. Expression Difference Mapping on PROTEINCHIP Arrays

Weak cationic exchange chromatography protein arrays (WCX2 PROTEINCHIP arrays; Ciphergen®, Fremont, Calif.) were loaded onto a 96-well bioprocessor, and equilibrated with 50 mM sodium acetate/0.1% octyl glucoside (Sigma, St. Louis, Mo.), pH 5.0. Forty µl anion exchange chromatography fraction was diluted into 100 µl of the same buffer on each array spot, and incubated for an hour. Array spots were washed 3 min with 100 µl 50 mM sodium acetate/ 0.1% octyl glucoside pH 5. After rinsing with water, 2×1 µl of sinapinic acid solution were added per array spot.

D. Protein Profiling with SELDI-TOF MS

Arrays were read using the Protein Biology System II SELDI-TOF mass spectrometer (Ciphergen®, Fremont, Calif.). The reader was externally calibrated daily using peptide standard calibrants of known molecular weights (Ciphergen®, Fremont, Calif.).

E. Processing of SELDI-TOF Mass Spectra

Spectra were processed with the PROTEINCHIP Software Biomarker Edition, Version 3.2.0 (Ciphergen, Fremont, Calif.) After baseline subtraction, spectra were normalized by means of total ion current method Peak detection was performed with the Biomarker Wizard software (Ciphergen, Fremont, Calif.) employing a signal-to-noise ratio of 3.

F. Protein Marker Identification

Protein markers were purified by affinity chromatography on IgG spin column and by reverse phase chromatography. Purity of each step was monitored by Normal Phase PROTEINCHIP Array. The main fractions were reduced by 5 mM DTT pH9 and alkylated with 50 mM iodoacetamide in the dark for 2 h. The final separation was on a 16% Tricine SDS PAGE gel. The gel was stained by Colloidal Blue Staining Kit (Invitrogen). Selected protein bands were excised, washed with 200 μl of 50% methanol/10% acetic acid for 30 min, dehydrated with 100 μl of ACN for 15 min, and extracted with 70 μl of 50% formic acid, 25% ACN, 15% isopropanol, 10% water for 2 hrs at room temperature with vigorous shaking. Protein marker in extract was verified by analysis of 2 μl a Normal Phase PROTEINCHIP Array. Remaining extract was digested by 20 μl of 10 ng/ul of modified trypsin (Roche Applied Science) in 50 mM ammonium bicarbonate (pH 8) for 3 hrs at 37° C.

Single MS and MS/MS spectra were acquired on a QSTAR mass spectrometer equipped with a Ciphergen PCI-1000 PROTEINCHIP Interface. A 1 μl aliquot of each protease digest was analysed on a NP20 PROTEINCHIP Array in the presence of CHCA.

Spectra were collected from 0.9 to 3 kDa in single MS mode. After reviewing the spectra, specific ions were selected and introduced into the collision cell for CID fragmentation. The CID spectral data was submitted to the database-mining tools Mascot (Matrix Sciences) for identification.

Example 2

Identifying Biomarkers Using SELDI

This example describes how the present invention may be used to identify useful biomarkers for diagnosing, or determining the prognosis after treatment of, a patient.

To identify biomarkers useful in practicing the present invention, reference biomarker profiles are first established for two populations of patients. One population acts as the "control" group, expressing a first phenotype. The second population is a "test group" displaying the phenotype whose diagnosis through detection of a biomarker is sought. In this example, the test group are individuals that were afflicted or where subsequently (within six months) afflicted with a tumor that displayed metastatic potential during the course of the study. The control group is from a population that did not manifest any cancerous affliction of any type for at least twelve months subsequent to completion of the study.

Biomarkers between the populations are identified by comparing expression of biomolecules isolated from platelets. Preparation of blood samples for testing are as described below. The platelet homogenates formed are sequentially profiled on Q10, IMAC30-Cu(II) and CM10 SELDI probe PROTEINCHIP arrays. Biomarkers are identified by differential levels of expression of one or more of platelet-associated biomolecules from the homogenate as determined by the area beneath the peak(s) formed for the ion species produced by the biomarker(s). Statistical analysis are then performed on the data to assure the changes in biomarker expression levels are both significant and correlate accurately with the metastatic cancer.

Example 3

Using Biomarkers to Predict Prognosis of a Cancer Patient During Treatment

This example illustrates the use of biomarkers to determine the prognosis of a cancer patient after treatment to alleviate the cancer.

Blood samples are taken from a patient to be assessed at one or more different times during the course of assessment, for example at days 0, 2, 5, 10, 14, 21, 30, 60 and/or 90 days. Blood samples are preferably assessed while fresh, but may be stored frozen until a suitable time for assessment. Assessment of the patient begins on the first day the patient arrives at the hospital or clinic, and continues for at least several weeks after treatment for the cancerous condition has ceased.

Analysis of the blood samples is carried out by first isolating platelets and creating a platelet homogenate suitable for testing. Platelets are isolated from individual blood samples using established procedures well known to those of skill in the art. Platelet extracts are then prepared by suspending the isolated platelets in ice-cold isotonic buffer (1 vol platelets: 3 vol of buffer solution), then sonicating the platelet suspension for fifteen seconds. Each platelet extract is then fractionated using by ion-exchange beads (Q HyperD) and assayed on WCX2 PROTEINCHIP arrays. The proteins retained on the arrays are detected by SELDI mass spectroscopy and the amounts of each ion species quantified by determining the area beneath the ion peak produced. Results are tabulated and the amounts of biomarkers corresponding to BF4 and CTAP III determined for each sample.

The tabulated results are then used to establish the prognosis of the patient. Prognosis is determined by comparing the relative amounts of BF4 and CTAPIII-related ion species from each sample. For patients undergoing therapy to treat an aggressive cancerous tumor, an increase in the measured biomarker levels indicates that the tumor has ceased aggressive invasion into new tissue environments and is now dormant. In this situation the patient is periodically monitored after treatment for any future decrease in marker levels indicative of the tumor returning to an aggressive phenotype.

For patients undergoing surgical removal of an aggressive tumor, patient are assessed for relapse beginning several weeks after treatment. The time lapse is necessary to allow biomarker fluxuations cause by the surgical procedure, independent of the tumor being removed, to settle. Under these circumstances, successful removal of the tumor is accompanied by a disappearance of the BF4 and CTAP III markers.

It is understood that the examples and embodiments described herein are for illustrative purposes only and that various modifications or changes in light thereof will be suggested to persons skilled in the art and are to be included s, patents, and patent applications cited herein are hereby incorporated by reference in their entirety for all purposes.

What is claimed is:

1. A method for determining a change in endogenous angiogenic activity of a subject, the method comprising:
    (a) detecting expression of one or more platelet-associated biomarkers in a platelet sample from the subject, wherein expression of at least one detected biomarker is modified in relation to the change in endogenous angiogenic activity; and
    (b) correlating the expression of at least one detected biomarker with the change in endogenous angiogenic activity by comparing the expression of the detected biomarker with previously determined expression for the same biomarker,
    wherein the platelet-associated biomarker is selected from the group consisting of connective tissue activating protein III (CTAP III), apolipoprotein A1, and IL-8, and
    wherein the change in endogenous angiogenic activity of the subject is categorized as dormant, aggressive, sustained aggressive, regressive or no change.

2. The method according to claim 1, wherein the platelet-associated biomarker is connective tissue activating protein III (CTAP III).

3. The method according to claim 1, wherein the platelet-associated biomarker is apolipoprotein A1.

4. The method according to claim 1, wherein the platelet-associated biomarker is IL-8.

5. A method for determining a change in endogenous angiogenic activity of a subject, the method comprising:
  (a) detecting expression of one or more platelet-associated biomarkers in a platelet sample from the subject, wherein expression of at least one detected biomarker is modified in relation to the change in endogenous angiogenic activity;
  (b) correlating the expression of at least one detected biomarker with the change in endogenous angiogenic activity by comparing the expression of the detected biomarker with previously determined expression for the same biomarker;
  (c) managing subject treatment based on the categorized change in endogenous angiogenic activity; and
  (d) detecting the expression of a plurality of platelet-associated biomarkers after subject treatment, wherein the platelet-associated biomarker is selected from the group consisting of connective tissue activating protein III (CTAP III), apolipoprotein A1, and IL-8, and wherein the change in endogenous angiogenic activity of the subject is categorized as dormant, aggressive, sustained aggressive, regressive or no change.

\* \* \* \* \*